United States Patent
Carvalho de Sousa et al.

(10) Patent No.: US 12,276,596 B2
(45) Date of Patent: Apr. 15, 2025

(54) SYSTEMS, DEVICES, COMPONENTS AND METHODS FOR ANALYZING BODY FLUID SAMPLES

(71) Applicant: Labinlight Lda, Viana do Castelo (PT)

(72) Inventors: Nuno Jorge Carvalho de Sousa, Oporto (PT); Miguel Angelo Alves Gomes dos Santos Silva, Vila Nova de Gaia (PT); João Carlos Cruz de Sousa, Vila do Conde (PT); António César Silva Ferreira, Oporto (PT); João Alexandre Oliveira Martins, Vila Nova de Gala (PT); António Manuel Pacheco e Murta, Braga (PT); Vitor Manuel da Rocha Dinis, Viana do Castelo (PT)

( * ) Notice: Subject to any disclaimer, the term of this patent is extended or adjusted under 35 U.S.C. 154(b) by 916 days.

(21) Appl. No.: 17/222,911

(22) Filed: Apr. 5, 2021

(65) Prior Publication Data
US 2021/0315496 A1   Oct. 14, 2021

(30) Foreign Application Priority Data

Apr. 8, 2020   (EP) .................................... 20168719

(51) Int. Cl.
*A61B 5/15*   (2006.01)
*A61B 5/00*   (2006.01)
(Continued)

(52) U.S. Cl.
CPC ....... *G01N 21/0303* (2013.01); *A61B 5/0075* (2013.01); *B01L 3/50* (2013.01); *G01N 2021/0385* (2013.01); *G01N 33/487* (2013.01)

(58) Field of Classification Search
CPC ............ A61B 5/150343; A61B 5/0075; A61B 5/15182; A61B 5/150412;
(Continued)

(56) References Cited

U.S. PATENT DOCUMENTS

| 5,223,219 A | 6/1993 | Subrananian et al. |
| 5,523,054 A | 6/1996 | Switalski |

(Continued)

FOREIGN PATENT DOCUMENTS

| EP | 21167207.6 | 7/2021 |
| WO | WO 97/25608 | 7/1997 |
| WO | WO 2016/065115 | 4/2016 |

OTHER PUBLICATIONS

Texas Instruments, User's Guide, DLP® NIRscan™ Nano EVM, Literature No. DLPU030F, Jun. 2015, revised Mar. 2016, pp. 1-100, Dallas, Texas, USA.

(Continued)

*Primary Examiner* — Hoa Q Pham
(74) *Attorney, Agent, or Firm* — Woods Patent Law, P.C.

(57) ABSTRACT

Disclosed are devices, components and methods associated with a body fluid analysis system, which, according to some embodiments, can be employed in at-home, clinical, medical office and outpatient settings and applications. The system can be configured to provide results within a short period of time after a body fluid sample has been acquired from a patient such as by a finger or skin prick. In some embodiments, a body fluid sample cartridge is configured for use in conjunction with a corresponding spectroscopic body fluid analysis device, where the cartridge comprises one or more body fluid dispersing sheets, layers or membranes. In some embodiments, the cartridge is configured to deliver and disperse a predetermined amount or volume of a body fluid sample taken from a human or animal onto, into, through or across the body fluid dispersing sheet, layer or membrane disposed within the cartridge for subsequent analysis of the body fluid sample by a corresponding spectroscopic device.

95 Claims, 15 Drawing Sheets

(51) Int. Cl.
*B01L 3/00* (2006.01)
*G01N 21/03* (2006.01)
*G01N 33/487* (2006.01)

(58) Field of Classification Search
CPC ........ A61B 5/150358; A61B 5/150022; G01N 33/743; G01N 33/689; G01N 33/558; G01N 33/49; G01N 21/6428; G01N 21/6486; G01N 2021/0346
USPC ......... 356/301–326, 246, 440, 39–41; 435/5, 435/6.12, 28, 18, 7.92, 29, 7.94, 287.2, 435/288.7, 287.3; 436/501; 422/69, 422/82.05, 82.01, 119; 600/300, 368, 600/324, 326
See application file for complete search history.

(56) References Cited

U.S. PATENT DOCUMENTS

| | | |
|---|---|---|
| 2006/0228259 A1 | 10/2006 | Samsoondar |
| 2006/0257991 A1* | 11/2006 | McDevitt ............... C12M 41/36 435/287.2 |
| 2008/0038738 A1* | 2/2008 | Weigum ............. A61B 5/14535 435/6.12 |
| 2008/0180658 A1 | 7/2008 | Samsoondar |
| 2012/0257188 A1 | 10/2012 | Yan |
| 2014/0335505 A1* | 11/2014 | Holmes .................. G16H 10/40 435/6.12 |
| 2017/0203295 A1* | 7/2017 | Bau-Madsen .......... G01N 21/05 |
| 2018/0037929 A1 | 2/2018 | Martins et al. |

OTHER PUBLICATIONS

Corranet et al., Dried blood spots as a source of anti-malarial . . . studies, 2008, Sep. 30, 2008, Malaria Jour., 7:195, pp. 1-12, BioMed Central, London, U.K.

GE Healthcare UK, Typical Data—Grade 1—Qualitative Filter, 2019, pp. 1-2, General Electric Company, Buckinghamshire, U.K.

Jonsman Innovation, HydroPLA Hydrophilic polymer, 2021, pp. 1-3, Joinn ApS, Gørløse, Denmark.

Jones, The Impact of Contact Angle on the Biocompatibility of Biomaterials, 2010, pp. 387-399, Opt. & Vision Sci., vol. 87, No. 6.

Sedlock, Hydrophilicity and surface energy, a little of the Science behind the test strip, p. 2018, pp. 1-4, 3M Medical Materials & Technologies.

* cited by examiner

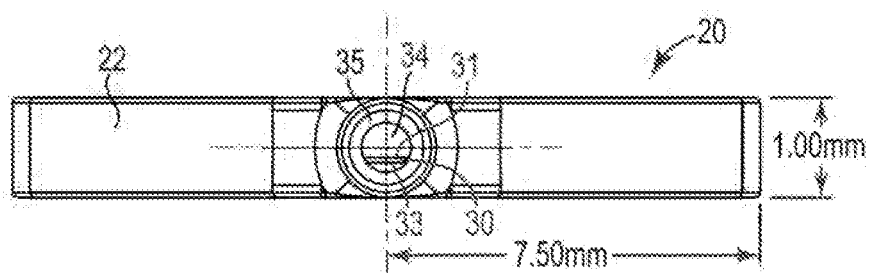
Fig. 4(b)
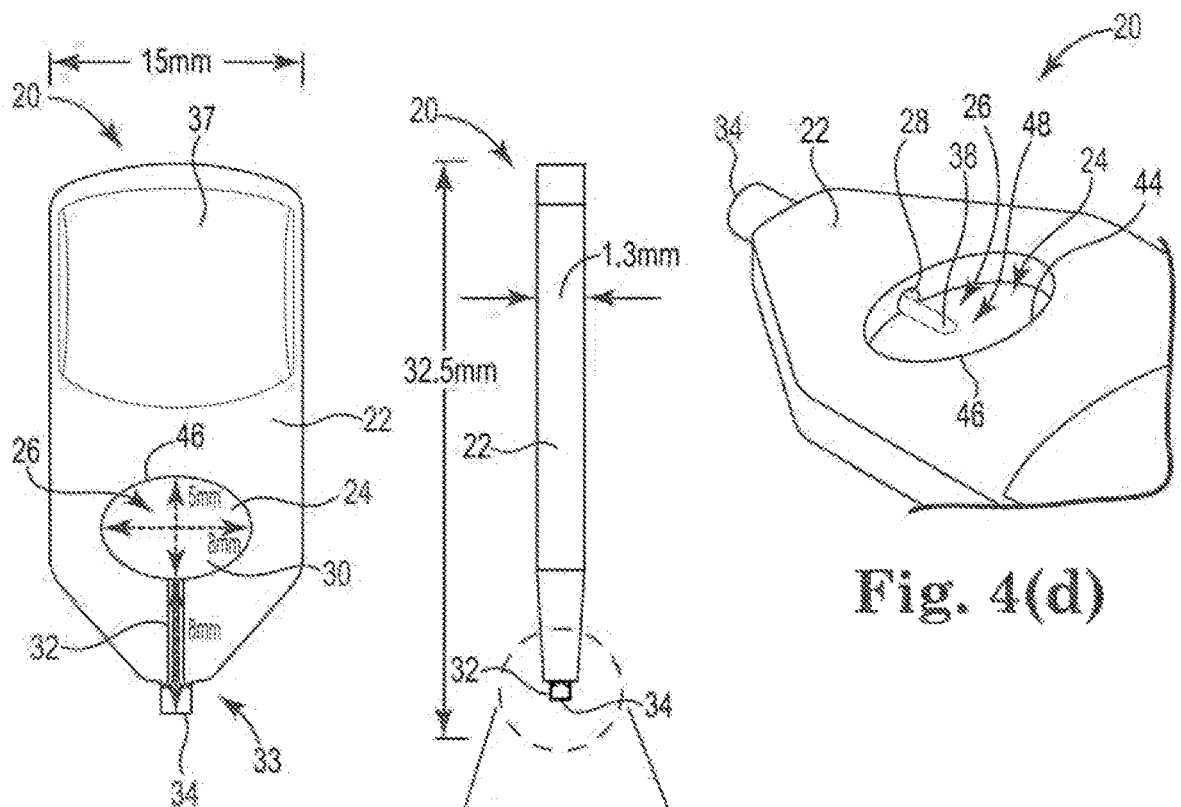
Fig. 4(d)
Fig. 4(a)
Fig. 4(c)
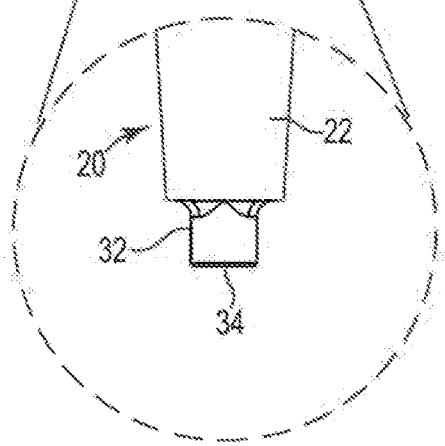

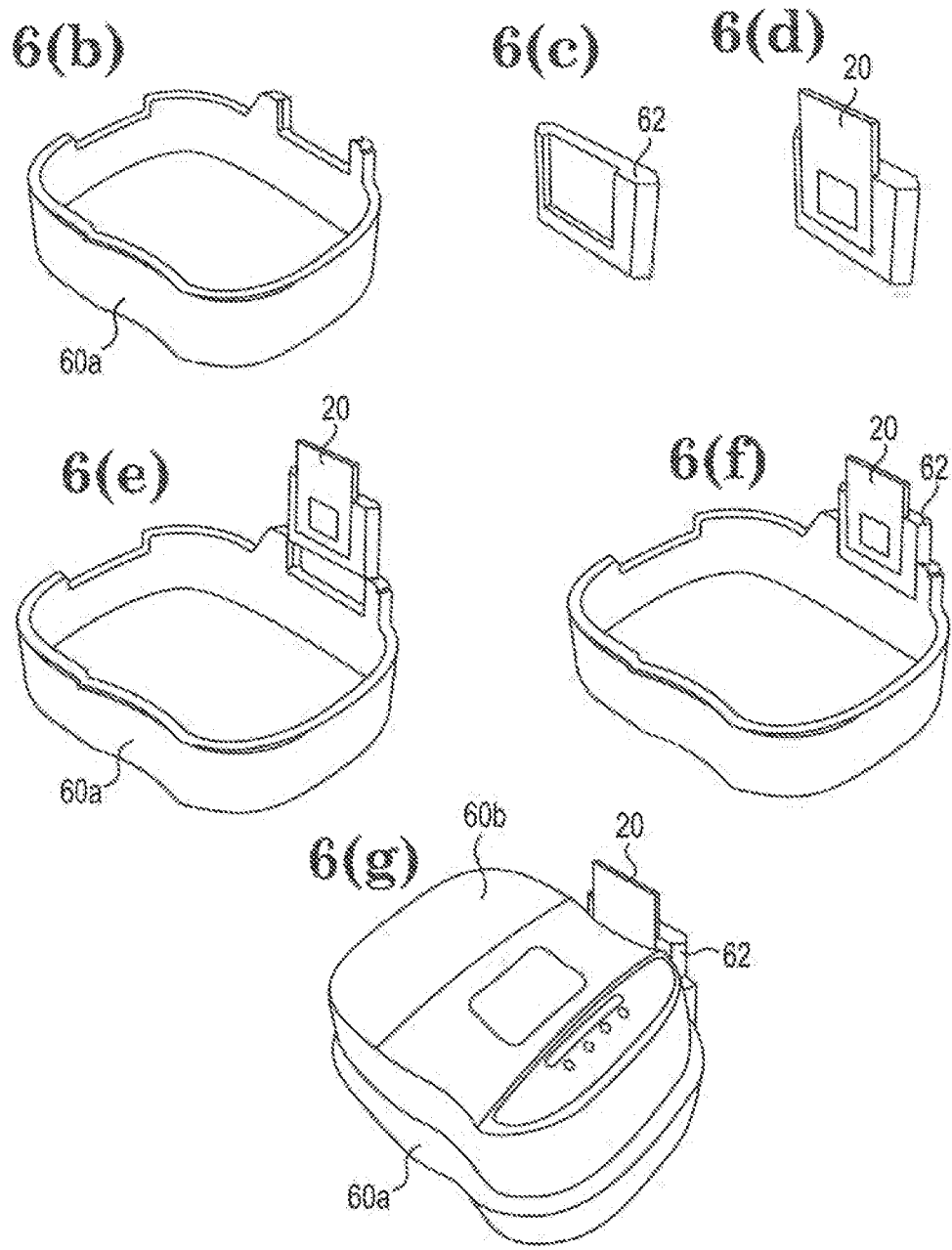

SELF-REGULATING VOLUME

PROLONGED CONTACT

| | m (g) | 9uL : 20uL | | 11uL : 20uL | |
|---|---|---|---|---|---|
| EMPTY CARTRIDGE | 0.809 | MEAN | 10 | MEAN | 10 |
| CARTRIDGE WITH W1 | 0.8119 | STD | 2 | STD | 1 |
| W1 | 0.0029 | MAX | 12.6 | MAX | 12.6 |
| | | MIN | 6.3 | MIN | 8.4 |
| | | DENSITY (BLOOD) = 1kg/m3 | | | |
| | | HTC=25% | VDROP | m (g) | V (uL) |
| m1 | 0.8143 | | 9 | 0.0063 | 6.3 |
| m2 | 0.8083 | | 11 | 0.0084 | 8.4 |
| m3 | 0.7996 | | 13 | 0.0100 | 10.0 |
| m4 | 0.8069 | | 15 | 0.0104 | 10.4 |
| m5 | 0.8026 | | 20 | 0.0114 | 11.4 |
| | | HTC=47.3% | VDROP | m (g) | V (uL) |
| m6 | 0.8103 | | 9 | 0.0083 | 8.3 |
| m7 | 0.8098 | | 11 | 0.0095 | 9.5 |
| m8 | 0.8119 | | 13 | 0.0098 | 9.8 |
| m9 | 0.8091 | | 15 | 0.0120 | 12.0 |
| m10 | 0.8043 | | 20 | 0.0126 | 12.6 |
| | | HTC=71.8% | VDROP | m (g) | V (uL) |
| m11 | 0.8044 | | 9 | 0.0080 | 8.0 |
| m12 | 0.8037 | | 11 | 0.0096 | 9.6 |
| m13 | 0.8049 | | 13 | 0.0108 | 10.8 |
| m14 | 0.8141 | | 15 | 0.0091 | 9.1 |
| m15 | 0.8045 | | 20 | 0.0123 | 12.3 |

Fig. 8

SELF-REGULATING VOLUME

FINITE CONTACT

| | 9uL / 20uL | | |
|---|---|---|---|
| MEAN | | | 8 |
| STD | | | 1 |
| MAX | | | 10.0 |
| MIN | | | 7.4 |
| DENSITY (BLOOD) = 1 kg/m3 | | | |
| HTC=17% | Vdrop | m (g) | V (uL) |
| | 9 | 0.0074 | 7.4 |
| | 11 | 0.0082 | 8.2 |
| | 13 | 0.0082 | 8.2 |
| | 15 | 0.0085 | 8.5 |
| | 20 | 0.0100 | 10.0 |
| HTC=41% | Vdrop | m (g) | V (uL) |
| | 9 | 0.0078 | 7.8 |
| | 11 | 0.0084 | 8.4 |
| | 13 | 0.0075 | 7.5 |
| | 15 | 0.0084 | 8.4 |
| | 20 | 0.0089 | 8.9 |
| HTC=52% | Vdrop | m (g) | V (uL) |
| | 9 | 0.0079 | 7.9 |
| | 11 | 0.0083 | 8.3 |
| | 13 | 0.0087 | 8.7 |
| | 15 | 0.0089 | 8.9 |
| | 20 | 0.0089 | 8.9 |

SYSTEMS, DEVICES, COMPONENTS AND METHODS FOR ANALYZING BODY FLUID SAMPLES

RELATED APPLICATIONS

This application is related to, and claims priority and other benefits from, European Patent Application EP20168719 entitled "Cartridge for Spectroscopic Device for Quantification in Biological Fluids, Respective Kit and Manufacturing Method Thereof" filed with the EPO on Apr. 8, 2020 (hereafter "the '8719 European patent application"). The entirety of the '8719 patent application is hereby incorporated by reference herein, a complete copy of which is filed on even date herewith in an Information Disclosure Statement.

FIELD OF THE INVENTION

Various embodiments described and disclosed herein relate to the field of medicine generally, and more particularly to body fluid analysis devices, components and methods which, according to some embodiments, can be employed in at-home, clinical, medical office, and outpatient settings and applications.

BACKGROUND

Techniques exist that have been proven to be effective for the quantification of parameters relating to biological fluids, such as, for example, the Siemens ADVIA 120 Hematology System™. However, the ADVIA 120 Hematology System, which among others can be considered a gold reference standard, is expensive, immobile, bulky, and requires 175 μL of sample volume using a venipuncture collection method. It also requires reagents and consumables, operation by trained health professionals, and is not easily applied to point-of-care settings located outside of hospital conditions, such as in, for example, home, clinical, medical office, outpatient settings and applications, emergency situations, military scenarios or in underdeveloped countries having poor medical infrastructures. A few portable blood analysis solutions do exist, such as, for example, the HemoCuem™ system, but in at least some cases are only configured to provide hemoglobin-specific results.

What is needed are improved system, devices, components, means and methods for providing a portable or semi-portable blood analysis system that can be employed in at-home and other out-of-hospital and out-of-laboratory conditions, and that are capable of providing a range of blood analysis results quickly and on-site.

SUMMARY

In one embodiment, there is a provided a mammalian body fluid sample cartridge configured for use in conjunction with a corresponding spectroscopic mammalian body fluid analysis device, the spectroscopic device comprising at least one light source, at least one reflected light sensor, and at least one light transmission and light acquisition aperture, the cartridge comprising a cartridge frame or body; a cartridge opening or window disposed in the frame or body, the opening or window sized and shaped to operate in cooperation and in conjunction with the at least one light source, the at least one reflected light sensor, and the at least one aperture of the spectroscopic device; at least one body fluid dispersing sheet, layer or membrane disposed in or across at least portions of the cartridge opening or window, and at least one body fluid sample capillary tube or channel formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body, wherein the opening or window, the at least one body fluid dispersing sheet, layer or membrane, and the body fluid sample capillary tube and channel are together configured to deliver and disperse a predetermined amount or volume of a body fluid sample taken from a mammal and introduced to the tube or channel inlet at least one of onto, into, through and across the at least one body fluid dispersing sheet, layer or membrane for subsequent analysis of the body fluid sample by the corresponding spectroscopic device when the cartridge is placed or fitted in an operative position or location with respect to the corresponding spectroscopic device.

Such an embodiment may further comprise one or more of: (a) the body fluid sample comprising one or more of human or animal blood, menstrual blood, urine, saliva, semen, vaginal fluid, and sweat; (b) the body fluid sample being augmented by one or more of a liquid buffer, a reagent, a fluid viscosity alteration agent, and a solvent; (c) the cartridge and spectroscopic device being together configured, shaped and sized for use in at least one of at-home patient, clinical, medical office, and outpatient settings or applications; (d) after the body fluid sample has been dispersed onto the at least one sheet, layer or membrane, the body fluid sample becoming a dried fluid spot sample on the at least one sheet, layer or membrane; (e) the dried fluid spot sample being one of a dried blood spot (DBS), dried urine spot (DUS) and a dried saliva spot (DSS); (f) the predetermined amount or volume of the body fluid sample drawn onto the at least one dispersing sheet, layer or membrane ranging between about 3 μl and about 10 μl; (g) the predetermined amount or volume of the body fluid sample drawn onto the at least one dispersing sheet, layer or membrane ranging between about 2 μl and about 14 μl; (h) the predetermined amount or volume of the body fluid sample being acquired from a pool of bodily fluid taken from the mammal that ranges between about 2 μl and about 20 μl; (i) the predetermined amount or volume of the body fluid sample drawn onto the at least one dispersing sheet, layer or membrane being substantially evenly distributed and dispersed across the at least one sheet, layer or membrane; (j) the predetermined amount or volume of the body fluid sample drawn onto the at least one dispersing sheet, layer or membrane not completely saturating the at least one sheet, layer or membrane; (k) the at least one dispersing sheet, layer or membrane being absorbent; (l) the body fluid sample comprising human blood acquired by a skin or finger prick or through venipuncture of a patient; (m) the opening or window having a minimum width or diameter ranging between about 2 mm and about 8 mm, a maximum width or diameter ranging between about 3 mm and about 20 mm, and a sidewall height or depth to a bottom surface thereof ranging between about 0.25 mm and about 3 mm; (n) the tube or channel having a diameter ranging between about 0.25 mm and about 2.0 mm or a diameter ranging between about 0.5 mm and about 1.5 mm; (o) a surface area within the window or opening of the at least one dispersing sheet, layer or membrane ranging between about 10 mm2 and about 60 mm2; (p) the at least one dispersing sheet, layer or membrane comprising one or more of paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly(vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly(vinylidene fluoride), polyester, polycarbonate, cellulose acetate, cellulose nitrate, poly(vinyl chloride), and nylon; (q) the sheet, layer or membrane being configured to pull the body fluid sample thereacross or therethrough to near, at or beyond a perimeter of the window or opening; (r) the outlet of the tube or channel being disposed in a central or near-central portion of the opening or window such that the body fluid sample is dispersed initially from a location near or adjoining a center of the at least one sheet, layer or membrane; (s) the outlet of the tube or channel being located inside a perimeter of the window or opening and points towards or is located near or at a central or near-central bottom portion of the opening or window; (t) the sheet, layer or membrane being located above a bottom, side or sidewall surface of the opening or window, and the outlet of the tube or channel is disposed near or on the bottom surface of the window or opening, such that air and body fluid flow through the tube or channel into the opening and onto the sheet, layer or membrane is facilitated; (u) the spectroscopic device being a fluorescence spectrometer or being configured to operate in one or more of an infrared light spectrum, a near-infrared light spectrum, a visible light spectrum, and an ultraviolet light spectrum; (v) the cartridge and the spectroscopic device being together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device; (w) at least one of the tube or channel and frame or body comprising a polymer, a plastic and a polymeric material; (x) the polymer or plastic of the tube or channel, or frame or body, being at least one of anticoagulant-free, heparin-free, and comprising a polylactic acid (PLA) bioplastic; (y) the tube or channel inlet comprising a material or a coating characterized by a low contact angle when placed in contact with a body fluid; (z) the tube or channel outlet comprising a material or a coating characterized by a low contact angle when in contact with a body fluid (aa) prior to introduction of the body fluid sample to the at least one sheet, layer or membrane, no reactive or body fluid contaminating materials, chemicals, additives or constituents being disposed in or on the cartridge or selected portions thereof; (bb) the at least one dispersing sheet, layer or membrane comprising a material exhibiting a low spectral absorbance; (cc) the cartridge being configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device; (dd) the opening or window being at least one of elliptical in shape, circular in shape, rectangular in shape, square in shape, triangular in shape, and non-circular in shape; (ee) the cartridge comprising a grippable or matingly engageable structural feature or element disposed on a portion thereof, the structural feature or element being configured to facilitate human or machine handling of the cartridge; (ff) further comprising a cap, container or bag configured to seal at least portions of the cartridge to prevent contamination of the body fluid sample disposed therein; (gg) further comprising or having associated therewith a machine-readable label or unique identifier comprising or providing access to information regarding the body fluid sample disposed in the cartridge; (hh) the cartridge being sized, shaped and configured for handling, processing, and analysis of the body fluid sample in a laboratory; (ii) the cartridge being configured and shaped for use with a corresponding wet or chemical analysis tube or receptacle; and (jj) the cartridge being configured and shaped to permit the at least one sheet, layer or membrane to be cut or removed from the cartridge and extracted therefrom.

In another embodiment, there is provided a method of spectroscopically analyzing a mammalian body fluid sample contained in a cartridge configured for use in conjunction with a corresponding spectroscopic mammalian body fluid analysis device, the spectroscopic device comprising at least one light source, at least one reflected light sensor, and at least one light transmission and light acquisition aperture, the cartridge comprising a cartridge frame or body and a cartridge opening or window disposed in the frame or body, the opening or window sized and shaped to operate in conjunction with the at least one light source, the at least one reflected light sensor, and the at least one aperture of the spectroscopic device, at least body fluid dispersing sheet, layer or membrane being disposed in or across at least portions of the cartridge opening or window, a body fluid sample capillary tube or channel being formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body, wherein the opening or window, the at least one body fluid dispersing sheet, layer or membrane, and the body fluid sample capillary tube or channel are together configured to deliver and disperse a predetermined or near-predetermined amount or volume of a body fluid sample taken from a mammal and introduced to the tube or channel inlet at least one of onto, into, through and across the at least one body fluid dispersing sheet, layer or membrane for subsequent analysis of the body fluid sample by the corresponding spectroscopic device when the cartridge is placed or fitted in an operative position or location with respect to the corresponding spectroscopic device, the method comprising obtaining or acquiring the body fluid sample; placing the tube or channel inlet of the cartridge in, on, or near the body fluid sample such that the predetermined amount or volume of the body fluid sample is delivered and dispersed at least one of onto, into, through and across the at least one dispersing sheet, layer or membrane; placing the cartridge in an operative position with respect to the corresponding spectroscopic device, and analyzing the body fluid sample contained in the cartridge with the corresponding spectroscopic device.

Such an embodiment may further comprise one or more of: (a) the spectroscopic device being fluorescence spectrometer or being configured to perform one or more of near-infrared spectroscopy, infrared spectroscopy, ultraviolet spectroscopy, visible light spectroscopy, and mass spectroscopy on the body fluid sample in the cartridge; (b) the body fluid sample comprising human or animal blood, and the analysis further comprises one or more of determining amounts, percentages, volumes or predictions of one or more of levels of oxygen, nutrients, waste, electrolytes, glucose, urea, total proteins, proteins, albumins, triglycerides, hematocrits, hemoglobins, complete blood count, circulating tumor cells, tumor markers, CA 15.3 markers, TRU-QUANT and CA 27.29 markers, CA125 markers, CEA (carcinoembryonic antigen) markers, viruses, and pathologies associated with, contained in, or detectable in the body fluid sample; (c) further comprising augmenting or adding augmented one or more of a liquid buffer, a reagent, a fluid viscosity alteration agent, and a solvent to the body fluid sample; (d) the body fluid sample comprising a human body fluid, and the analysis further comprises one or more of determining characteristics of the body fluid sample for forensic or criminal investigation purposes; (e) the cartridge and spectroscopic device being together configured, shaped and sized for use in at least one of at-home patient, clinical, medical office, and outpatient settings or applications; (f) after the body fluid sample has been dispersed onto the at least one sheet, layer or membrane, the body fluid sample becoming a dried fluid spot sample on the at least one sheet, layer or membrane; (g) the dried fluid spot sample being one of a dried blood spot (DBS), dried urine spot (DUS) and a dried saliva spot (DSS); (h) the predetermined amount or volume of the body fluid sample drawn onto the at least one dispersing sheet, layer or membrane ranging between about 3 µl and about 10 µl; (i) the predetermined amount or volume of the body fluid sample drawn onto the at least one dispersing sheet, layer or membrane ranging between about 2 µl and about 14 µl; (j) the predetermined amount or volume of the body fluid sample drawn onto the at least one dispersing sheet, layer or membrane ranging between about 2 µl and about 20 µl; (k) the predetermined amount or volume of the body fluid sample drawn onto the at least one dispersing sheet, layer or membrane being substantially evenly distributed and dispersed across the at least one sheet, layer or membrane; (l) the predetermined amount or volume of the body fluid sample drawn onto the at least one dispersing sheet, layer or membrane not completely saturating the at least one sheet, layer or membrane; (m) further comprising pricking a skin or a finger of a human patient or animal, or performing a venipuncture, to acquire the body fluid sample; (n) the at least one dispersing sheet, layer or membrane comprising one or more of paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly(vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly(vinylidene fluoride), polyester, polycarbonate, cellulose acetate, cellulose nitrate, poly(vinyl chloride), and nylon; (o) the sheet, layer or membrane being configured to pull the body fluid sample thereacross or therethrough to near, at or beyond a perimeter of the window or opening; (p) the outlet of the tube or channel being disposed in a central or near-central bottom portion of the opening or window such that the body fluid sample is dispersed initially from a location near or adjoining a center of the at least one sheet, layer or membrane; (q) the outlet of the tube or channel being located inside a perimeter of the window or opening and points towards or is located near or at a central or near-central bottom portion of the opening or window; (r) the sheet, layer or membrane being located above a bottom, side or sidewall surface of the opening or window, and the outlet of the tube or channel is disposed near or on the bottom surface of the window or opening, such that air and body fluid flow through the tube or channel into the opening and onto the sheet, layer or membrane is facilitated; (s) the spectroscopic device being a fluorescence spectrometer or being configured to operate in one or more of an infrared light spectrum, a near-infrared light spectrum, a visible light spectrum, and an ultraviolet light spectrum; (t) the cartridge and the spectroscopic device being together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device; (u) the tube or channel inlet comprising a material characterized by a low contact angle when placed in contact with a body fluid; (v) the tube or channel outlet comprising a material characterized by a low contact angle when in contact with a body fluid; (w) prior to introduction of the body fluid sample thereto, no reactive or body fluid contaminating materials, chemicals, additives or constituents being disposed in or on the cartridge or selected portions thereof; (x) the at least one dispersing sheet, layer or membrane comprising a material exhibiting a low spectral absorbance; (y) the cartridge being configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device; (z) the cartridge comprising a grippable or matingly engageable structural feature or element disposed on a portion thereof, the structural feature or element being configured to facilitate human or machine handling of the cartridge; (aa) further comprising sealing or capping at least portions of the cartridge to prevent contamination of the body fluid sample disposed therein; (bb) further comprising providing a machine-readable label or unique identifier having information regarding the body fluid sample disposed in the cartridge; (cc) further comprising providing the cartridge to a laboratory for wet or chemical analysis of the body fluid sample; (dd) the cartridge being configured and shaped for use with a corresponding wet analysis tube or receptacle; (ee) the cartridge being configured and shaped to permit the at least one sheet, layer or membrane to be cut or removed from the cartridge and extracted therefrom; and (ff) the body fluid sample contained in the cartridge being analyzed by the corresponding spectroscopic device within a time period of one or more of less than about 120 seconds, less than about 60 seconds, less than about 45 seconds, less than about 30 seconds, and less than about 15 seconds after the body fluid sample has been drawn into the cartridge.

In yet another embodiment, there is provided a system for spectroscopically analyzing a mammalian body fluid sample, the system comprising a spectroscopic body fluid analysis device, the device comprising at least one light source, at least one reflected light sensor, and the at least one light transmission and light acquisition aperture, at least one corresponding cartridge configured for use in conjunction with the spectroscopic body fluid analysis device, the cartridge comprising a cartridge frame or body, a cartridge opening or window disposed in the frame or body, the opening or window being sized and shaped to operate in conjunction with the at least one light source, the at least one reflected light sensor, and the at least one aperture of the spectroscopic device, at least one body fluid dispersing sheet, layer or membrane being disposed in or across at least portions of the cartridge opening or window, and a body fluid sample capillary tube or channel formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body; wherein the opening or window, the at least one body fluid dispersing sheet, layer or membrane, and the body fluid sample capillary tube or channel are together configured to deliver and disperse a predetermined amount or volume of a body fluid sample taken from a mammal and introduced to the tube or channel inlet at least one of onto, into, through and across the at least one body fluid dispersing sheet, layer or membrane for subsequent analysis of the body fluid sample by the spectroscopic device when the corresponding cartridge is placed or fitted in an operative position or location with respect to the spectroscopic device.

Such an embodiment may further comprise one or more of: (a) the body fluid sample being augmented by one or more of a liquid buffer, a reagent, a fluid viscosity alteration agent, and a solvent; (b) the cartridge and spectroscopic device are together configured, shaped and sized for use in at least one of at-home patient, clinical, medical office, and outpatient settings or applications; (c) the predetermined amount or volume of the body fluid sample drawn onto the at least one dispersing sheet, layer or membrane ranging between about 3 µl and about 10 µl; (d) the predetermined amount or volume of the body fluid sample drawn onto the at least one dispersing sheet, layer or membrane ranging between about 2 µl and about 14 µl; (e) the predetermined amount or volume of the body fluid sample being acquired from a pool of bodily fluid taken from the mammal that ranges between about 2 µl and about 20 µl; (f) the predetermined amount or volume of the body fluid sample drawn onto the at least one dispersing sheet, layer or membrane being substantially evenly distributed and dispersed across the at least one sheet, layer or membrane; (g) the predetermined amount or volume of the body fluid sample drawn onto the at least one dispersing sheet, layer or membrane not completely saturating the at least one sheet, layer or membrane; (h) the body fluid sample comprising human blood acquired by a skin or finger prick or through venipuncture of a patient; (i) the spectroscopic device being a fluorescence spectrometer or being configured to operate in one or more of an infrared light spectrum, a near-infrared light spectrum, a visible light spectrum, and an ultraviolet light spectrum; (j) the cartridge and the spectroscopic device being together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device; (k) at least one of the tube or channel and frame or body comprising a polymer, a plastic and a polymeric material; (l) the polymer or plastic of the at least one of the tube or channel or frame or body is at least one of anticoagulant-free, heparin-free, and comprises a polylactic acid (PLA) bioplastic; (m) the cartridge being configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device; (n) further comprising a cap, container or bag configured to seal at least portions of the cartridge to prevent contamination of the body fluid sample disposed therein; (o) further comprising or having associated therewith a machine-readable label or unique identifier comprising or providing access to information regarding the body fluid sample disposed in the cartridge; (p) the cartridge being sized, shaped and configured for handling, processing, and analysis of the body fluid sample in a laboratory; (q) the cartridge being configured and shaped for use with a corresponding wet or chemical analysis tube or receptacle; and (r) the cartridge being configured and shaped to permit the at least one sheet, layer or membrane to be cut or removed from the cartridge and extracted therefrom.

Further embodiments are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

FIGS. 4(a) through 4(f) show various views of one embodiment of a body fluid sample cartridge 20;

FIGS. 6(a) through 6(g) show selected portions of one embodiment of a spectroscopic device 60 and associated cartridge 20;

FIG. 8 shows further body fluid volumetric test results obtained using prolonged contact with blood samples and one embodiment of cartridge 20;

The drawings are not necessarily to scale. Like numbers refer to like parts or steps throughout the drawings.

DETAILED DESCRIPTIONS OF SOME EMBODIMENTS

Described and disclosed herein are various embodiments of systems, devices, components and methods relating to body fluid analysis which, according to some embodiments, can be employed in at-home, clinical, medical office, and outpatient settings and applications.

Some embodiments described and disclosed herein relate to a re-usable or disposable cartridge configured for use with a near-infrared or infrared spectroscopic device for quantification and analysis of associated with biological fluids, such as human or animal body fluids.

Figure 1:
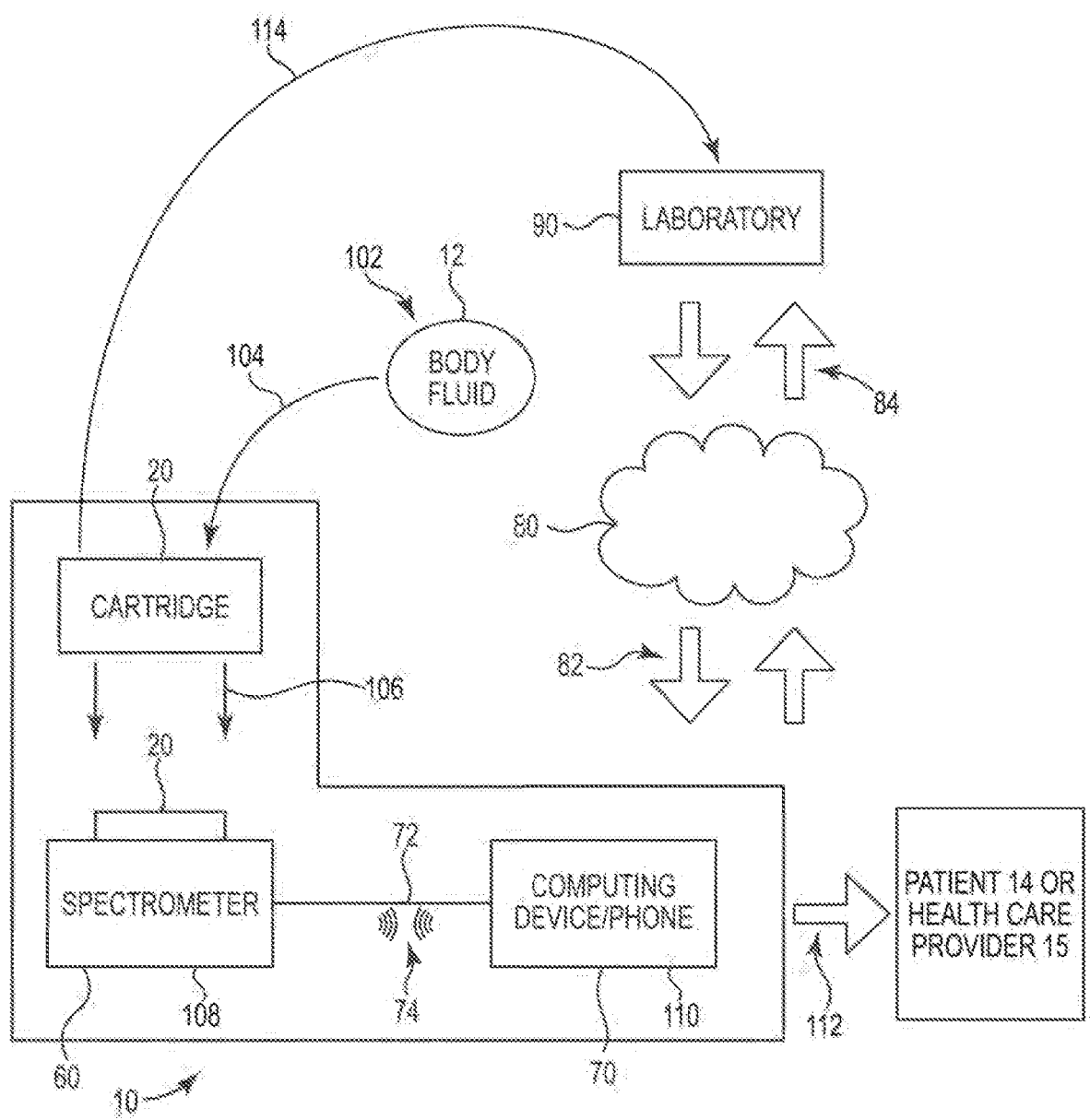
FIG. 1 shows a schematic diagram illustrating various methods, aspects and features according to one embodiment of a body fluid acquisition and analysis system 10.

Referring now to FIG. 1, there is shown a schematic diagram illustrating various methods, aspects and features according to one embodiment of a body fluid acquisition and analysis system 10, which is configured to analyze, quantify, measure, or otherwise characterize one or more parameters associated with a body fluid or body fluid sample 12. Body fluid or body fluid sample may be obtained from a human, animal or other subject, such as a human patient 14. By way of non-limiting example, body fluid or body fluid sample 12 may comprise one or more of human or animal blood, menstrual blood, urine, saliva, semen, vaginal fluid, sweat, serum, plasma, cerebrospinal fluid, or any other suitable biological or body fluid obtained from a human or animal.

In some embodiments, and by way of non-limiting example, body fluid or body fluid sample 12 may be acquired or obtained by the patient themselves, by a medically untrained person, by a health care professional such as a nurse or doctor, a veterinarian or veterinarian's assistant, or a device configured to acquire or obtain the body fluid or body fluid sample 12 from the patient or animal. For example, in some embodiments cartridge 20 may be configured to include a retractable, deployable, or other pricking device or means incorporated into or onto, or engageable or mateable with, cartridge 20. In some embodiments, body fluid or body fluid sample 12 may comprise human or animal blood acquired by a skin or finger prick or through venipuncture of a patient. In some embodiments, the body fluid sample may be augmented by one or more of a liquid buffer, a reagent, a fluid viscosity alteration agent, and a solvent to facilitate uptake of the body fluid or body fluid sample into cartridge 20.

Figure 2:
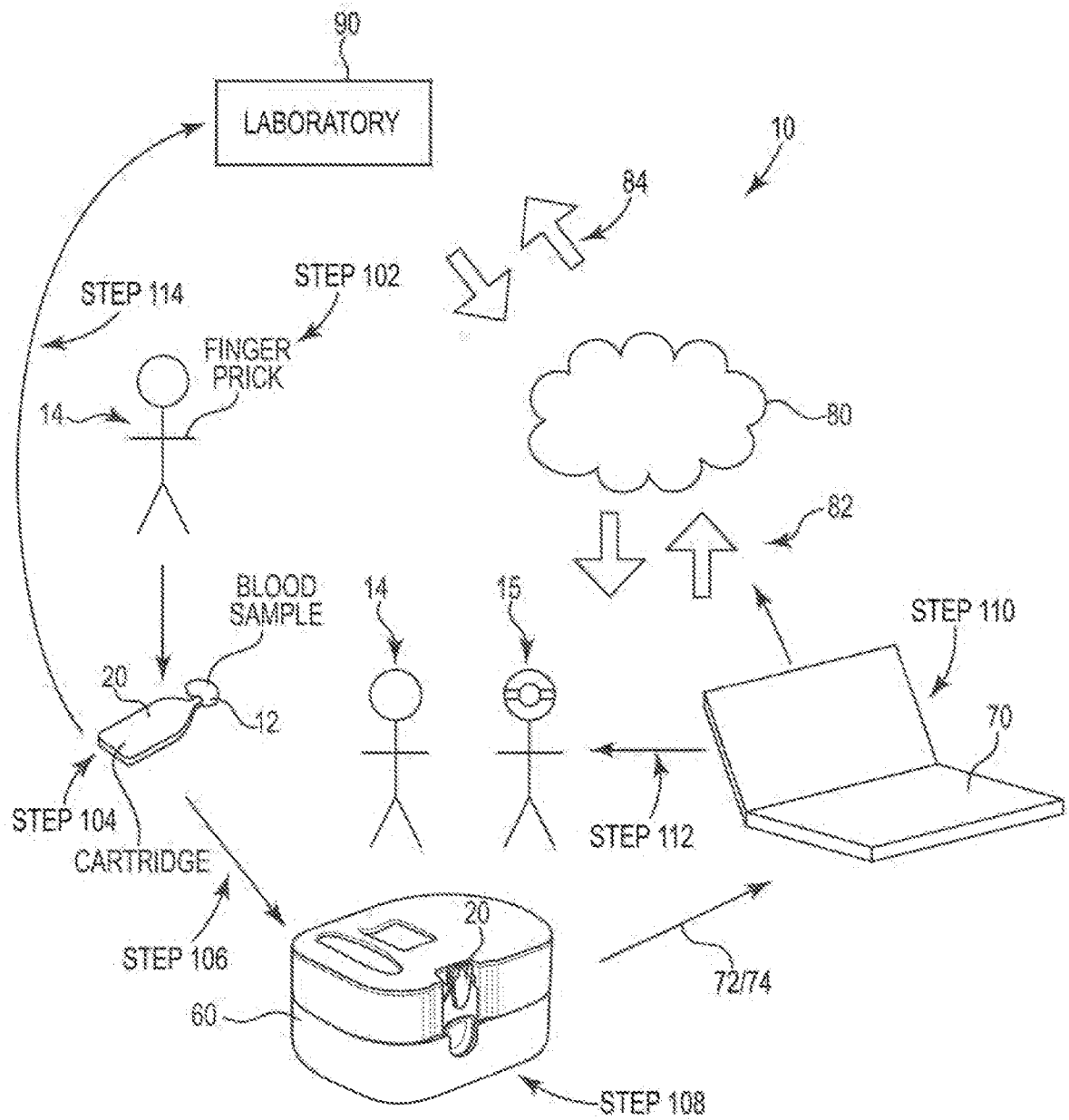
FIG. 2 shows a schematic diagram illustrating various methods, aspects and features according to another embodiment of a body fluid acquisition and analysis system 10.
Figure 5:
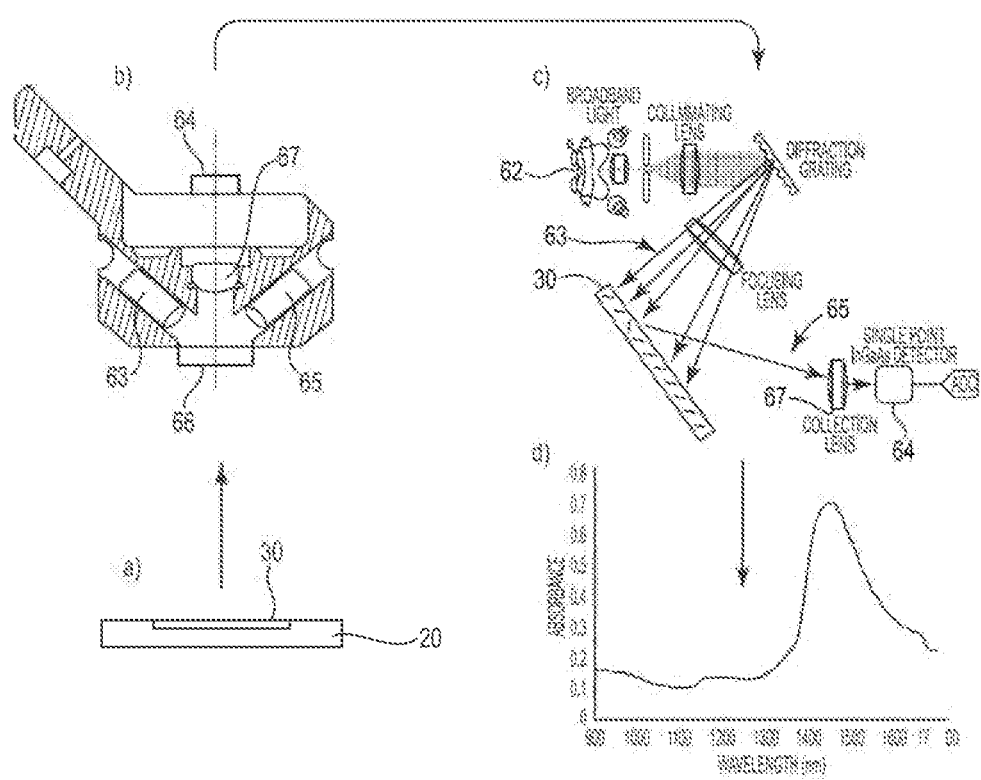
FIG. 5 shows schematic diagrams associated with one embodiment of a near-infrared (NIR) spectroscopic device 60 and associated body fluid cartridge 20 of system 10.

Referring now to FIGS. 1, 2 and 5, and in some embodiments, cartridge 20 and spectroscopic device 60 are together configured, shaped and sized for use in at least one of at-home patient, clinical, medical office, and outpatient settings or applications, more about which is said below. Thus, in some embodiments, spectroscopic device 20 is of relatively small size and hand-carriable or portable. Once body fluid or body fluid sample 12 has been sampled using cartridge 20 and drawn onto or into sheet, layer or membrane 30 thereof (as further described below), cartridge 20 is inserted into spectrometer or spectroscopic device 60, where the body fluid 12 on or in sheet, layer or membrane 30 is subjected to one or more illumination beams emitted by at least one light source 62 of spectroscopic device 60 through one or more light transmission and light acquisition apertures 66 thereof and onto sheet, layer or membrane 30. The incident light beams are then reflected off sheet, layer or membrane 30 through the one or more apertures for detection and acquisition by at least one reflected light sensor 64 in spectroscopic device 60 (see FIG. 7).

In some embodiments, spectroscopic device 60 of system 10 is configured to operate in one or more of an infrared light spectrum, a near-infrared light spectrum, a visible light spectrum, and an ultraviolet light spectrum. Infrared spectroscopy relies on absorption of light by molecules.

In some embodiments, spectroscopic device 60 is configured to perform one or more of near-infrared spectroscopy, infrared spectroscopy, ultraviolet spectroscopy, visible light spectroscopy, and mass spectroscopy on body fluid sample 12 in cartridge 20.

In one illustrative embodiment that is not intended to be limiting, spectroscopic device 60 is a DLP® NIRscan™ Nano EVM spectroscopic device manufactured by Texas Instruments, of Dallas, Tex., US, and is configured to operate in the near-infrared light spectrum. The entirety of a User's Manual entitled "User's Guide, DLP® NIRscan™ Nano EVM," Literature Number DLPU030F, dated June 2015 and revised March 2016 describing such a device 60, filed on even date herewith in an Information Disclosure Statement (IDS), is hereby incorporated by reference herein.

In another embodiment, device 60 is configured to operate as a fluorescent spectroscopy device (e.g., as a fluorimetry or spectrofluorometry device) such that device 60 is capable of analyzing the fluorescence of body fluid sample 12 held by cartridge 20. In such an embodiment, device 60 uses a beam of light, such as ultraviolet light, that excites the electrons in molecules of certain compounds contained in the body fluid sample 12 of cartridge 20, and causes them to emit light, typically, but not necessarily, in the visible light spectrum. A complementary technique is absorption spectroscopy. In the case of single molecule fluorescence spectroscopy, intensity fluctuations from the emitted light are measured from either single fluorophores, or pairs of fluorophores.

Devices configured to measure fluorescence can also be called fluorometers, of which there are two main types: filter fluorometers (which use filters to isolate the incident light from fluorescent light) and spectrofluorometers (which use diffraction grating monochromators to isolate the incident light from fluorescent light). Both types use light from an excitation source that passes through a filter or monochromator, and strikes the body fluid sample 12. A proportion of the incident light is absorbed by sample 12, and some of the molecules in the sample fluoresce. Some of this fluorescent light passes through a second filter or monochromator and reaches a detector, which is usually placed at 90° to the incident light beam to minimize the risk of transmitted or reflected incident light reaching the detector.

Regardless of the light spectrum over which system 10 and spectroscopic device 60 are configured to operate, and in some embodiments, cartridge 20 and spectroscopic device 60 are together configured such that the cartridge 20 is configured and shaped to permit reproducible and accurate registration and location of sheet, layer or membrane 30 (and thereby also cartridge 20) with respect to one or more incoming light beams 63 emitted by a light source 62, and one or more outgoing light beams 65 reflected from sheet, layer or membrane 30 and detected by spectroscopic device 60 by light detector 64.

Continuing to refer to FIGS. 1, 2 and 5, spectroscopic device 60 is configured to process at least some of the information and/or signals acquired by light detector 64 to produce, by way of non-limiting example, absorbance vs. wavelength results corresponding to the body fluid sample 12 of cartridge 20 and layer, sheet or membrane 30 (as shown at the bottom-right of FIG. 7), or any other suitable results that can be measured and provided by spectroscopic device 60, as is well known by those skilled in arts of spectroscopy and body fluid analysis. For instance, and by way of non-limiting example, attenuated total reflectance (ATR) and/or Fourier transform infrared (FTIR) spectroscopy techniques may be employed for the detection and discrimination of human blood, saliva, semen, vaginal secretions, and other body fluids. ATR FT-IR spectroscopy can detect and distinguish between such body fluids based on the unique spectral pattern, combination of peaks and peak frequencies corresponding to the macromolecule groups common within a given biological material. Comparisons with known abundant proteins or other biological parameters relevant to each body fluid can also be analyzed to enable specific peaks to be attributed to relevant characteristics, which can further reinforce accurate discrimination and identification of body fluids, viruses, proteins, and so on.

In some embodiments, and by way of non-limiting example, results provided by spectroscopic device 60 can be analyzed using one or more processors disposed within device 60, or using computing device 70, or both, to one or more of determine amounts, percentages, volumes or predictions of one or more of levels of oxygen, nutrients, waste, electrolytes, glucose, urea, total proteins, proteins, albumins, triglycerides, hematocrits, hemoglobins, complete blood count, biomarkers, brain natriuretic peptide (BNP) (see CAS #: 114471-18-0, a biomarker for heart failure), galectin-3 (gal-3, a biomarker for the diagnosis cardiovascular disease), Type III Procollagen Peptide (PIIINP, a biomarker to assess hepatic fibrosis), trimethylamine N-oxide (TMAO, see CAS #: 1184-78-7, a biomarker for the risk for major adverse cardiovascular events), cells, enzymes, lipids, carbohydrates, nucleic acids, circulating tumor cells, tumor markers, CA 15.3 markers, TRU-QUANT and CA 27.29 markers, CA125 markers, CEA (carcinoembryonic antigen) markers, viruses, and pathologies associated with, contained in, or detectable in body fluid or body fluid sample 12.

The foregoing are merely examples of chemicals, proteins, biological markers or substances, and the like that may be detected and analyzed using the methods, systems, devices, and components described and disclosed herein, and are not intended to be limiting or all-encompassing.

Further details regarding specific or particular algorithms, calculations, methods, or techniques that can be employed to process and analyze spectrographic data acquired by spectrometer 60, and to provide the above-described results, amounts, percentages, volumes, and/or predictions, are well known to those skilled in the art of body fluid spectroscopy.

Note that computing and analysis of results provided by spectroscopic device 60 can also be performed or supplemented by an appropriately configured tablet, smart phone or iPhone having a suitable app or other type of program loaded or incorporated therein, and which may be configured to communicate with spectroscopic device 60 through a dongle, via Bluetooth, a hardwired connection, or otherwise. In some embodiments, computing device 70 is a tablet, laptop, or desktop computer, and/or server. In other embodiments, computing device 70 is a smart phone or similar device. In still other embodiments, computing device 70 is a combination of a handheld or portable computing device such as a smart phone or tablet, and a laptop computer, desktop computer, server or other computer or computing device. Analysis of spectroscopic results can also be carried out or supplemented by a remote computer server or computer accessible via the Internet or the cloud 80. As shown in FIGS. 1 and 2, communication between spectrometer or spectroscopic device 60 and computing device or phone 70 may be enabled by communication via a hardware link 72 or a wireless or Bluetooth communication link 74.

Figure 3:
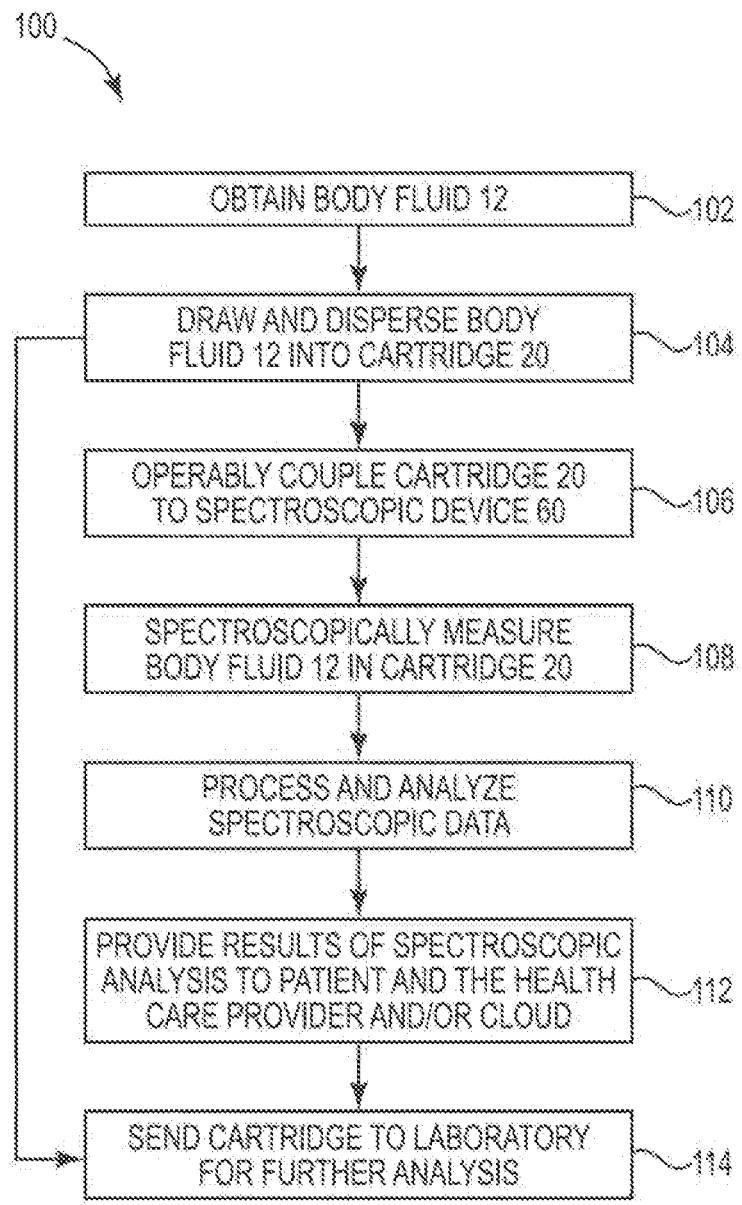
FIG. 3 shows one embodiment of a method 100 of a body fluid acquisition and analysis system 10.

Referring now to FIGS. 1, 2 and 3, and in some embodiments, spectroscopic results generated by computing device 70 can be provided to patient 14 and/or health care professional 15 on-site. See, for example, steps 102 through 114 of method 100 illustrated in FIG. 3. At step 102 body fluid 12 is obtained or acquired from a human patient 14 or animal. At step 104 body fluid 12 is drawn into and dispersed onto sheet, layer, or membrane 30 of cartridge 20. At step 106 cartridge 20 is next inserted or otherwise operably coupled to spectroscopic device 60. At step 108 body fluid 12, cartridge 20 is spectroscopically analyzed in spectroscopic device 60. At step 110, the spectroscopic results are processed and analyzed in any one or more of spectroscopic device 60, computing device 70, and/or cloud/remote server or computer 80. At step 112, the results of the spectroscopic analysis of body fluid 12 are provided to one or more of patient 14, health care professional 15, computing device 70, and/or cloud 80.

At optional step 114, cartridge and/or sheet, layer or membrane 30 is sent to a laboratory (e.g., a blood analysis laboratory) for further analysis of the body fluid sample 12 disposed in cartridge 12 by way of e.g., wet or chemical analysis involving, for example, placement of sheet, layer or membrane 30 in a vial or tube with a suitable chemical or mix of chemicals or fluids disposed therein that permit or enable further laboratory analysis of the sheet, layer or membrane 30). A cap, container or bag configured may be provided that seals at least portions of cartridge 20 to prevent contamination of body fluid sample 12 disposed therein during shipping to a laboratory for further analysis. Cartridge 20 may also further comprise or have associated therewith a machine-readable label or unique identifier comprising or providing access to information regarding the body fluid sample 12 disposed therein, such as the spectroscopic results generated by spectroscopic device 60 and/or computing device 70. Moreover, cartridge 20 may be sized, shaped and/or configured for handling, processing, and analysis of body fluid sample 12 in a laboratory to which cartridge 20 or sheet, layer or membrane 30 is sent, and may also be configured and shaped for use with a corresponding wet or chemical analysis tube or receptacle, or to permit the at least one sheet, layer or membrane 30 to be cut or removed from cartridge 20 and extracted therefrom for subsequent analysis in a laboratory.

Figure 4E:
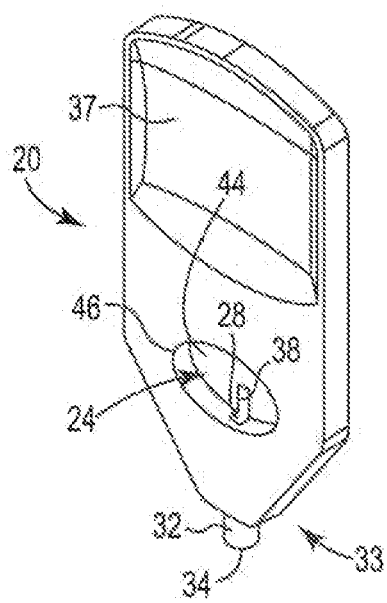
Figure 4F:
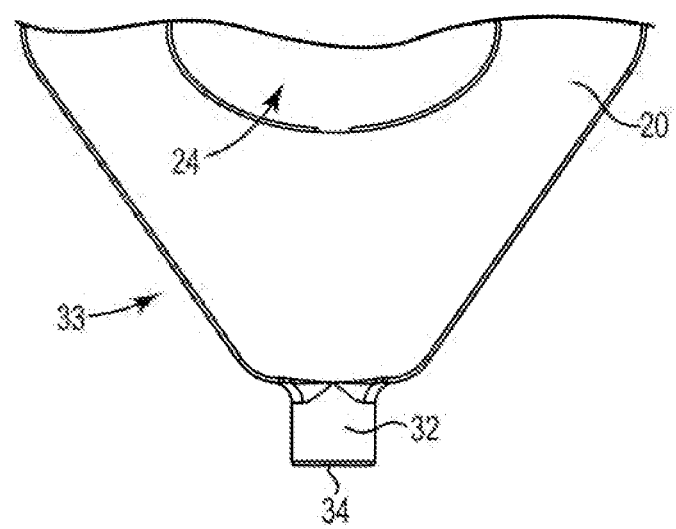

Referring now to FIGS. 4(a) through 4(f), there are shown various views of one embodiment of a mammalian body fluid sample cartridge 20. FIG. 4(a) shows a top plan view of one embodiment of cartridge 20. FIG. 4(b) shows an end bottom view of the cartridge of FIG. 4(a). FIG. 4(c) shows a left side view of the cartridge of FIG. 4(a). FIG. 4(d) shows a top right perspective view of a portion of cartridge 20 of FIG. 4(a). FIG. 4(e) shows a top right perspective view of cartridge 20 of FIG. 4(a). FIG. 4(f) shows an enlarged view of distal portion 33 of cartridge 30.

Continuing to refer to FIGS. 4(a) through 4(f), the embodiment of cartridge 20 shown and illustrated therein, which is not intended to be limiting, will be seen to comprise cartridge frame or body 22, cartridge opening or window 24, cartridge well or recess 26, cartridge sidewall 28, at least one body fluid dispersing sheet, layer or membrane 30, top surface 31 of body fluid dispersing sheet, layer or membrane 30, bottom surface 33 of body fluid dispersing sheet, layer or membrane 30, body fluid sample capillary tube or channel 32, body fluid collection inlet 34, body fluid dispersion outlet 38, bottom surface 44 of opening or window 24, perimeter 46 of window or opening 24. Certain illustrative dimensions of one embodiment of cartridge 20 (which dimensions are merely representative and not intended to be limiting), are shown in FIGS. 4(a), 4(b) and 4(d).

Continuing to refer to FIGS. 4(a) through 4(f), it will be seen that the embodiment of cartridge 20 shown and illustrated therein is a mammalian body fluid sample cartridge 20 configured for use in conjunction with a corresponding spectroscopic mammalian body fluid analysis device 60 as described above. The spectroscopic device 60 may comprise at least one light source 62, at least one reflected light sensor

64, and at least one light transmission and light acquisition aperture 66 (see, for example, FIG. 5).

In some embodiments, and as illustrated in FIGS. 4(*a*) through 4(*f*) and FIG. 5, cartridge 20 comprises cartridge frame or body 22, cartridge opening or window 24 disposed in frame or body 22, where opening or window 24 is sized and shaped to operate in cooperation and in conjunction with the at least one light source 62, the at least one reflected light sensor 64, and the at least one aperture 66 of the spectroscopic device 60. At least one body fluid dispersing sheet, layer or membrane 30 is disposed in or across at least portions of cartridge opening or window 24, and at least one body fluid sample capillary tube or channel 32 is formed or situated in or on a portion of cartridge frame or body 22. Tube or channel 32 comprises a body fluid collection inlet 34, which in one embodiment is disposed adjacent to an exterior portion of frame or body 22, and a body fluid dispersion outlet 38, which in one embodiment is disposed adjacent to a portion of opening or window 24 in frame or body 22, and as shown in FIG. 4(*d*) at or near a bottom of opening or window well 26. Note that in FIGS. 4(*d*) and 4(*e*), layer, sheet or membrane 30 is not shown in opening or window 24 so that the bottom of well 26 and outlet 38 of tube or channel 32 may be visualized by the reader.

In some embodiments, layer, sheet or membrane 30 is disposed between upper and lower portions or sections of frame or body 22 that are configured to hold, squeeze, or crimp layer, sheet or membrane 30 in place and prevent movement thereof. There are, however, numerous means by which layer, sheet or membrane 30 may be held in position within or on cartridge 20, such as, by way of non-limiting example, crimping, using adhesives, overmolding, configuring a perimeter of layer, sheet or membrane 30 to have tabs or protrusions formed therein that fit into corresponding slots or holes in the sidewalls or top surface of body or frame 22, fitting layer, sheet or membrane 30 into a separate frame that is then joined to or fits within or over opening or window 24, and so on. In addition, cartridge 20 may be formed or configured so that frame or body 22 may be pried or taken apart to permit layer, sheet or membrane 30 to be removed therefrom to, for example, facilitate chemical or other testing of layer, sheet or membrane 30.

Still continuing to refer to FIGS. 4(*a*) through 4(*f*), and in one embodiment, opening or window 24, the at least one body fluid dispersing sheet, layer or membrane 30, and body fluid sample capillary tube and channel 32 are together configured to deliver and disperse a predetermined amount or volume of a body fluid sample 12 taken from a mammal (such as patient 14) and introduced to the tube or channel inlet 34 at least one of onto, into, through and across the at least one body fluid dispersing sheet, layer or membrane 30 for subsequent analysis of the body fluid sample 12 by corresponding spectroscopic device 60 when cartridge 20 is placed or fitted in an operative registration, position or location with respect to corresponding spectroscopic device 60.

In some embodiments, after body fluid sample 12 has been dispersed onto the at least one sheet, layer or membrane, the at least one sheet, layer or membrane is configured such that body fluid sample 12 becomes a dried fluid spot sample on the at least one sheet, layer or membrane 30. The dried fluid spot sample can be, by way of non-limiting example, one of a dried blood spot (DBS), a dried urine spot (DUS) and a dried saliva spot (DSS), or a dried spot of any suitable mammalian or human body fluid or secretion. Details and further information regarding dried blood spots (DBSs) can be found in the publication "Dried blood spots as a source of anti-malarial antibodies for epidemiological studies" to Corranet et al., Malaria Journal 2008, 7:195doi: 10.1186/1475-2875-7-195, Sep. 30, 2008, the entirety of which is hereby incorporated by reference herein, and a complete copy of which is filed on even date herewith in an Information Disclosure Statement.

In some embodiments, the predetermined amount or volume of the body fluid sample 12 drawn onto the at least one dispersing sheet, layer or membrane 30 ranges between about 3 µl and about 10 µl, between about 2 µl and about 14 µl, and/or between about 2 µl and about 20 µl. This is an important property of some embodiments of cartridge 20, as only minimal but controlled amounts of body fluid are required to obtain accurate, useful, and quick spectroscopic results and analyses for a patient and their physician or other health care professional.

In some embodiments, the predetermined amount or volume of the body fluid sample 12 drawn onto the at least one dispersing sheet, layer or membrane 30 is substantially evenly distributed and dispersed across the at least one sheet, layer or membrane 30, and/or does not completely saturate the at least one sheet, layer or membrane. Both properties (even distribution of the body fluid across the layer, sheet or membrane, and no oversaturation of the layer, sheet or membrane) help provide optimal spectroscopic results. The at least one dispersing sheet, layer or membrane 30 can also be configured to be not only dispersive, but also absorbent. Choice and selection of materials from which to form and make the at least one dispersing sheet, layer or membrane 30 are thus also important, some of which are described and listed below.

Continuing to refer to FIGS. 4(*a*) through 4(*e*), and in some embodiments, opening or window 24 of cartridge has a minimum width or diameter ranging between about 2 mm and about 8 mm, a maximum width or diameter ranging between about 3 mm and about 20 mm, and a sidewall height or depth to a bottom surface thereof ranging between about 0.25 mm and about 3 mm. See, for example, FIG. 4(*a*), where window or opening 24 is shown to have an oblong or elliptical shape and dimensions of 5 mm across vertically and 8 mm across horizontally to provide a surface area of about 31.8 mm$^2$, and FIG. 4(*d*), where the corresponding sidewall height is about 1.3 mm. Other dimensions, surface areas, and sidewall heights are of course contemplated, such as those described below and as described above in connection with FIGS. 4(*a*), 4(*b*) and 4(*c*).

In addition, and in some embodiments, tube or channel 32 shown in FIGS. 4(*a*)-4(*e*) can have a diameter ranging between about 0.25 mm and about 2.0 mm, and a diameter ranging between about 0.5 mm and about 1.5 mm. By way of non-limiting example, and in some embodiments, the surface area of layer, sheet, or membrane 30 within window or opening 24 can range between about 10 mm$^2$ and about 60 mm$^2$.

The at least one dispersing sheet, layer or membrane 32 can be formed of numerous different materials, including, but not limited to, one or more of all suitable grades of Whatman qualitative filter papers, Whatman No 3 MM paper, Whatman No 1 MM paper, glass or fiber paper, paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly(vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly(vinylidene fluoride), polyester, polycarbonate, cellulose acetate, cellulose nitrate, poly(vinyl chloride), and nylon. Other suitable materials known to those skilled in the art may also be employed to form sheet, layer, or membrane 30. In addition, sheet, layer or membrane 30 can comprise multiple sheets, layers, or membranes which may or may not be laminated or otherwise joined or attached to one another.

One non-limiting example of a suitable sheet, layer or membrane for use in cartridge 20 is Whatman Grade 1 qualitative filter paper with a medium retention and flow rate manufactured by GE Life Sciences, as further described in a data sheet entitled "Typical Data"-Grade 1-Qualitative Filter" published by the General Electric Company in 2019, the entirety of which is hereby incorporated by reference herein, and a complete copy of which is filed on even date herewith in an Information Disclosure Statement.

In further embodiments, sheet, layer or membrane 30 is configured to pull body fluid sample 12 thereacross or therethrough to near, at or beyond (i.e., exceeding) perimeter 46 of window or opening 24, thereby helping fill the surface area of sheet, layer or membrane 30 and optimize spectroscopic measurements taken using cartridge 20 having body fluid sample 12 disposed therein or thereon. See FIGS. 4(*a*) and 4(*d*) showing the outlines of perimeter 46.

Referring now to FIG. 4(*d*), in some embodiments outlet 38 of tube or channel 32 is disposed in a central or near-central bottom portion 48 of opening or window 24 such that body fluid sample 12 is dispersed initially from a location near or adjoining a center of the at least one sheet, layer or membrane 30. As shown in FIG. 4(*d*), and according to one embodiment, outlet 38 of tube or channel 32 is located inside perimeter 46 of window or opening 24, and points towards or is located near or at a central or near-central bottom portion 48 of the opening or window. As shown in FIG. 4(*b*), and also according to one embodiment, sheet, layer or membrane 30 is located above bottom surface 44 of opening or window 24, and outlet 38 of tube or channel 32 is disposed near or on bottom surface 44 of window or opening 24 such that air and body fluid 12 flow through tube or channel 32 into the opening and onto sheet, layer or membrane 30 is facilitated.

As noted above, an important consideration is that each of cartridges 20 be configured and shaped to permit reproducible and accurate registration and location of sheet, layer or membrane 30 thereof with respect to one or more incoming light beams emitted by, and one or more outgoing light beams reflected from sheet, layer or membrane 30 and detected by, spectroscopic device 60.

In some embodiments, at least one of tube or channel 32 and frame or body 22 comprises a polymer, a plastic and a polymeric material. In further embodiments, the polymer or plastic employed to form tube or channel 32 and/or frame or body 22 is at least one of anticoagulant-free or heparin-free, and comprises a polylactic acid (PLA) bioplastic.

One non-limiting example of a polymer for use in fabricating at least portions of cartridge 20 is a hydrophilic polymer manufactured by Jonsman Innovation ApS of Gørløse, Denmark, as further described in a data sheet entitled "HydroPLA Hydrophilic polymer" published by Jonsman Innovation in 2021, the entirety of which is hereby incorporated by reference herein, and a complete copy of which is filed on even date herewith in an Information Disclosure Statement.

It has been discovered that another consideration in the design and practical use of cartridge 20 is that in some embodiments tube or channel inlet 34 have a convex shape (see, for example, convex-shaped portion 35 of inlet 34 in FIG. 4(*b*)). In addition, inlet 34 or portions of inlet 34 of tube or channel 32, outlet 38 or portions of outlet 38 of tube or channel 32, and portions of channel 32 disposed between inlet 34 and outlet 38 may be formed of or include a coating of a material that is characterized by a low contact angle (i.e., having a high degree of wettability) with respect to body fluid 12. In some embodiments, such low contact angles can range between about 10 degrees and about 20 degrees, although in some embodiments other ranges of contact angles may also be suitable, including, but not limited to, between about 5 degrees and about 30 degrees, between about 10 degrees and about 30 degrees, and between about 12 degrees and about 18 degrees. Two non-limiting examples of suitable low contact angle materials are the above-described HydroPLA Hydrophilic polymer and polylactic acid (PLA) bioplastic. Other suitable hydrophilic polymers, materials and coatings for inlet 34, tube 32, and outlet 38 are also contemplated. Further details relating to contact angles between portions 30, 32, 34 and 38 of cartridge 20 may be found in the publications "The Impact of Contact Angle on the Biocompatibility of Biomaterials" to Jones et al., Optometry and Vision Science, vol. 87, no. 6, pp. 387-399, 2010 ("the Jones paper"), and "Hydrophilicity and surface energy, a little of the Science behind the test strip" to Sedlock et al., 3M Medical Materials & Technologies, 2018 ("the 3M paper"). Each of the Jones paper and the 3M paper is hereby incorporated by reference herein, each in its respective entirety, the Jones paper and 3M paper being cited in an IDS filed on even date herewith with complete copies of same being filed therewith.

Low contact angles help draw up body fluids into cartridge 20, and also help disperse body fluids onto sheet, layer or membrane 30 in an effective, quick, accurate, reproducible, and even manner. In some embodiments, the shape of tube inlet 34, and the material(s) from which inlet 34 is formed, can be configured to hinder, prevent, or stop the spilling of blood or other body fluid out of the cartridge after the blood or body fluid has been collected (e.g., characterized by a low contact angle). An appropriate convex-shaped tube inlet can also increase user safety during blood or body fluid collection by preventing the "smearing" of surfaces with blood or other body fluids. With a low contact angle (e.g., 10-20 degrees) between cartridge 20/tube inlet 34 on the one hand, and the blood or body fluid sample 12 on the other hand, in embodiments where cartridge 20 is characterized by a high degree of "wettability" as regards blood samples 12 (e.g., where an appropriate or suitable hydrophilic material or coating is employed to form at least one of tube 32, inlet 34, and outlet 38), a low contact angle facilitates continuous liquid capillarity, and helps prevent body fluids from spilling out of cartridge 20 after they have been collected. It will now be seen that tube or channel inlet 34, when it comprises a polymeric material or suitable coating having a low contact angle (or high wettability) with body fluid 12 facilitates capillary rise or uptake into tube or channel 32. The lower the contact angle, the higher the capillary pressure, and thus the stronger the capillary action to maximize body fluid uptake by cartridge 20 and distribution or dispersion of body fluid 12 on paper 30.

Prior to introduction of body fluid sample 12 onto the at least one sheet, layer or membrane 30, and in some embodiments, no reactive or body fluid contaminating materials, chemicals, additives or constituents are disposed in or on the cartridge or selected portions thereof. Doing so can help ensure the accuracy of spectroscopic measurements taken using the cartridge, as well as ensuring the accuracy of any subsequent chemical or other measurements that might be taken on sheet, layer or membrane 30 after the spectroscopic measurements have been completed (e.g., laboratory blood tests). To help optimize the accuracy of spectroscopic measurements, the at least one dispersing sheet, layer or membrane 30 may comprise a material exhibiting low spectral absorbance.

As regards spectroscopic device 60 and the use of cartridge 20 in conjunction therewith, cartridge 20 may be configured and shaped to place a top surface of sheet, layer or membrane 30 within about 0.4 mm to about 1.2 mm of at least one aperture 66 disposed in spectroscopic device 60, thereby to optimize signal-to-noise ratios of signals acquired by spectroscopic device 60. In the case of the above-described DLP® NIRscan™ Nano EVM spectroscopic device 60, that distance has been determined to be about 0.8 mm.

Referring now to FIG. 4(*a*), opening or window 24 may be at least one of elliptical in shape, circular in shape, rectangular in shape, square in shape, triangular in shape, non-circular in shape, or any other suitable shape. Other shapes and configurations of opening or window 24 are therefore contemplated. Also shown in FIG. 4(*a*) is a grippable or matingly engageable structural feature or element 37 disposed on a portion thereof, which is configured to facilitate human or machine handling of cartridge 20.

Figure 6A:
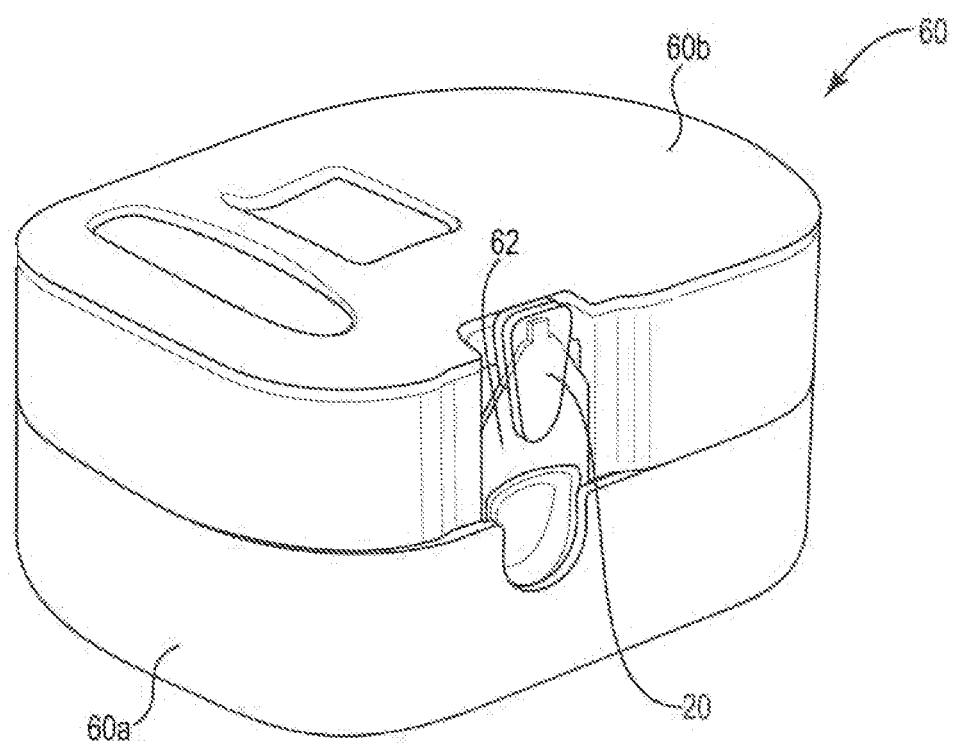

FIGS. 6(*a*) through 6(*g*) show various top left perspective views of upper and lower housings 60*a* and 60*b* of one embodiment of spectroscopic device 60, which features cartridge docking mechanism 62 for accepting cartridge 20 therein. Cartridge docking mechanism 62 is configured and shaped to permit reproducible and accurate registration and location of sheet, layer or membrane 30 (and thereby also cartridge 20) with respect to one or more incoming light beams 63 emitted by a light source 62, and one or more outgoing light beams 65 reflected from sheet, layer or membrane 30 and detected by spectroscopic device 60 by light detector 64.

Figure 7:
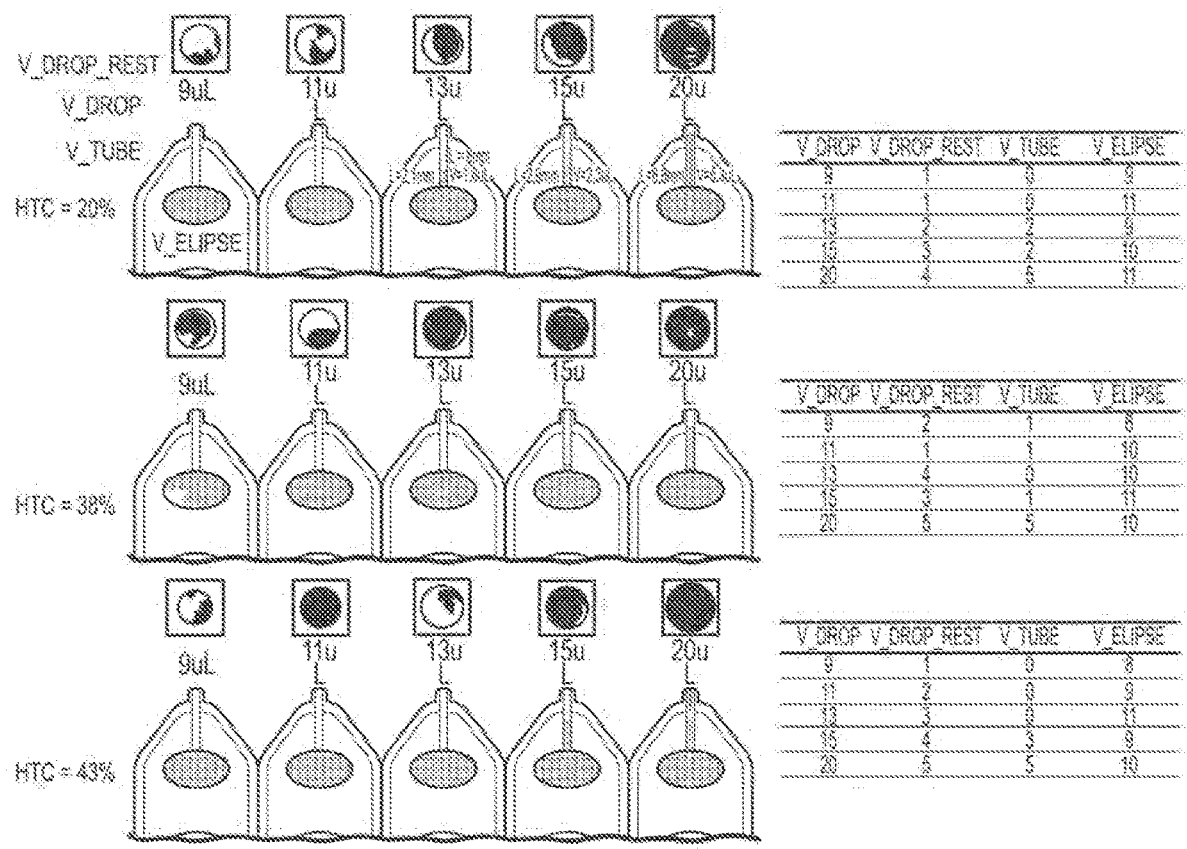
FIG. 7 shows body fluid volumetric test results obtained using prolonged contact with blood samples and one embodiment of cartridge 20.

FIGS. 7 and 8 show volumetric measurements carried out on cartridges 20 having the design and construction shown in FIGS. 4(*a*) through 4(*d*), and results obtained therewith for body fluid samples (in this case whole human blood samples) having varying levels of hematocrits (HTC), and varying volumes of the blood drops or samples from which body fluid samples were drawn into the cartridges and onto the sheets, layers, or membranes 30 thereof.

FIGS. 7 and 8 both illustrate the self-regulating volume properties of cartridge 20. FIGS. 7 and 8 show results obtained where each cartridge 20 touched a blood drop and remained in contact therewith during aspiration and uptake of blood sample 12 onto layers, sheets, or membranes 30 (which in this case was Whatman paper) until aspiration or uptake completely ceased (which we refer to here as "prolonged contact"). This blood sample collection method was found to cause an average variation of 10 uL±2 uL in uptake and dispersion onto sheet, layer or membrane 30. However, it was also discovered that if blood was collected only until cartridge tube 32 became filled (a method we call "finite contact"), greater volume control could be obtained, with an average variation of 8 uL±1 uL, more about which is said below in connection with FIGS. 10 and 11.

Data shown in FIG. 7 reflect self-regulated volume tests carried out on one embodiment of cartridges 20, where prolonged contact between cartridges 20 and drops of blood occurred. In FIG. 7, V_drop represents the volume of droplet available to be aspirated by cartridge 20. V_drop_rest, V_tube and V_ellipse are various different estimates of blood (more about which is said below), where the estimates were generated using photographs or images after blood had been drawn into cartridges 20. In FIG. 7, V_drop_rest is an estimate of the remaining volume of a blood drop following blood collection therefrom into a cartridge 20. V_tube is an estimate of the volume left in a tube of cartridge 20 after blood has been collected. V_ellipse is an estimate of the volume of blood that was absorbed by or dispersed through layer, sheet, or membrane 30 of cartridge 20.

In the left-hand column of the table shown on the right of FIG. 7, volumes of blood drops or samples are shown. In the right-hand column of FIG. 7, there are shown the resulting volumes of blood drawn onto the sheets, layers, or membranes 30 of cartridges 20. As will be seen by referring to the right-hand column of the table of FIG. 7, the volumes of blood drawn onto, dispersed and spread across sheets, layers, or membranes 30 of cartridges 20 are substantially and essentially independent of both hematocrit concentration and initial blood drop volume. These volume-regulating properties of cartridge 20 are further illustrated by referring to FIG. 8, where further data are shown.

While the data presented in FIG. 7 are estimates of values based on images as described above, the data in FIG. 8 refer to values based on actual measured masses of blood disposed on or in layer, sheet, or membranes 30 of cartridge 20 after different volumes of blood had been collected using such cartridges.

In FIG. 8, the first two columns list the masses of the 15 empty cartridges (m1:m15), and the masses of the paper 30 (inferred by the subtraction of the void by the "cartridge with w1"). This experiment employed using 3 different blood samples, which differed according to hematocrit concentration: i.e., HTC 25%, HTC 47.3% and HTC 71%. For each blood sample, 5 different blood drop volumes were provided to cartridge 20: 9 uL, 11 uL, 13 uL, 15 uL and 20 uL. One cartridge was used for each drop, and the blood was aspirated. Then, following blood 12 sample collection in each cartridge 20, the blood paper ellipse or layer 30 was removed and the mass was measured. This value was converted into a volume assuming a blood density of 1 kg/m$^3$. From there the exact blood volume collected onto layer 30 was calculated.

Reference to the right-most column of FIG. 8 shows that the volumes of blood actually collected onto sheets, layers or membranes 30 remained remarkably consistent regardless of the volume of the blood drop from which each body fluid sample 12 in cartridge 20 was drawn, and regardless of the hematocrit concentration of each such body fluid sample or drop. Thus, it will be seen that each cartridge was capable of dispersing a predetermined and reasonably accurate amount or volume of blood onto layers, sheets, or membranes 30 despite significant variations in initial blood drop size and hematocrit concentration.

Figure 9:
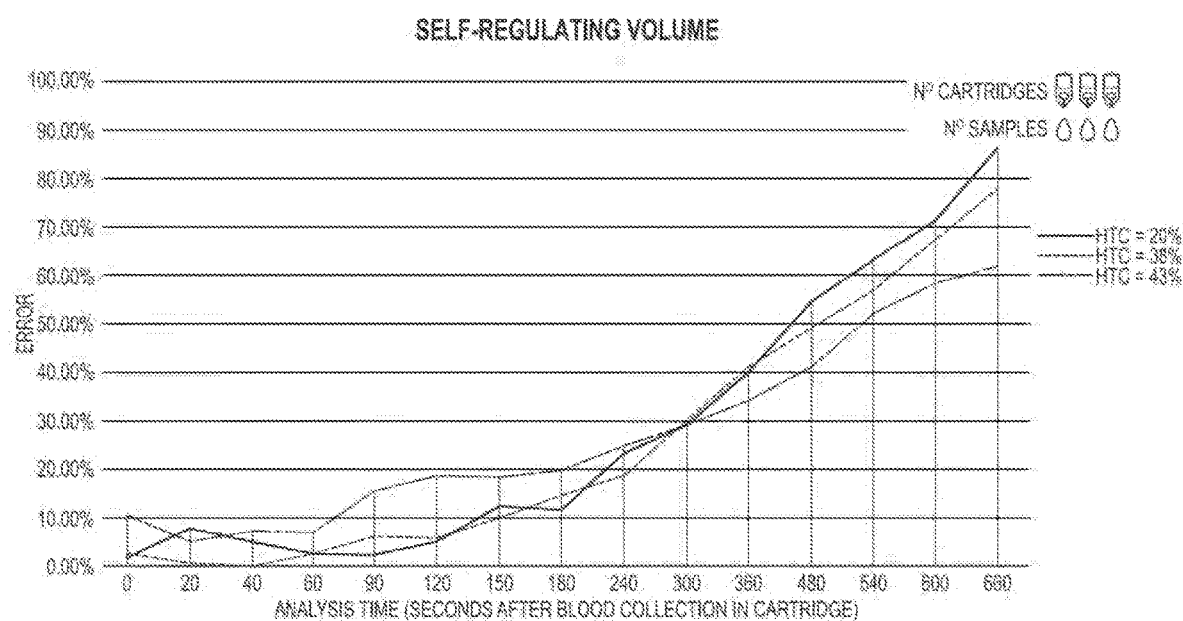
FIG. 9 shows error measurements obtained in a spectroscopic device 60 using cartridges 20 loaded with blood samples, where cartridges 20 were measured by spectroscopic device 60 at different time intervals after blood sample loading of cartridges 20.

FIG. 9 shows the results of an experiment which employed cartridges 20 identical to those employed in the experiments of FIGS. 7 and 8. In FIG. 9, 3 different types of blood drops having different hematocrit concentrations (i.e., HTC 25%, HTC 47.3% and HTC 71%) were drawn up into cartridges 20. For each blood drop or sample, a cartridge 20 was used to collect the blood 12, disperse it onto paper 30, and then presented to sensor 64 of device 60 immediately at t=0 seconds. The same cartridge, with exactly the same blood sample, was then measured in device 60 at 20-second intervals over a period of 660 seconds. The experiment was repeated for each of the remaining 2 blood samples having different hematocrit concentrations. Finally, a hemoglobin concentration prediction algorithm calculated the values for each spectrum acquired during the 660 second time period. The error of each predicted value was calculated against the real value, and resulted in the graph of FIG. 9, where error=(predicted value−actual value)/actual value.

Continuing to refer to FIG. 9, errors associated with spectroscopic measurements obtained using cartridges 20 having the design and construction shown in FIGS. 4(a) through 4(d) are shown, including results obtained for whole human blood samples having varying levels of hematocrits (HTC). FIG. 9 illustrates how errors in spectroscopic measurements increase rapidly with time after a cartridge 20 has been loaded with a blood sample and then subjected to spectroscopic measurement and analysis. As indicated by the results shown in FIG. 9, cartridges 20 should be measured and analyzed within 2 to 3 minutes of being loaded with a human blood sample if spectroscopic measurements are to be reasonably accurate, at least as regards cartridges 20 of the design and configuration employed to obtain the results shown in FIG. 9.

Figure 10:
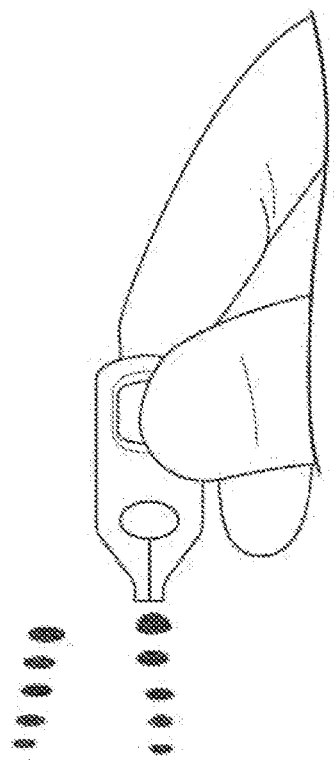
FIG. 10 shows body fluid volumetric test results obtained using finite contact with blood samples and one embodiment of cartridge 20.
Figure 11:
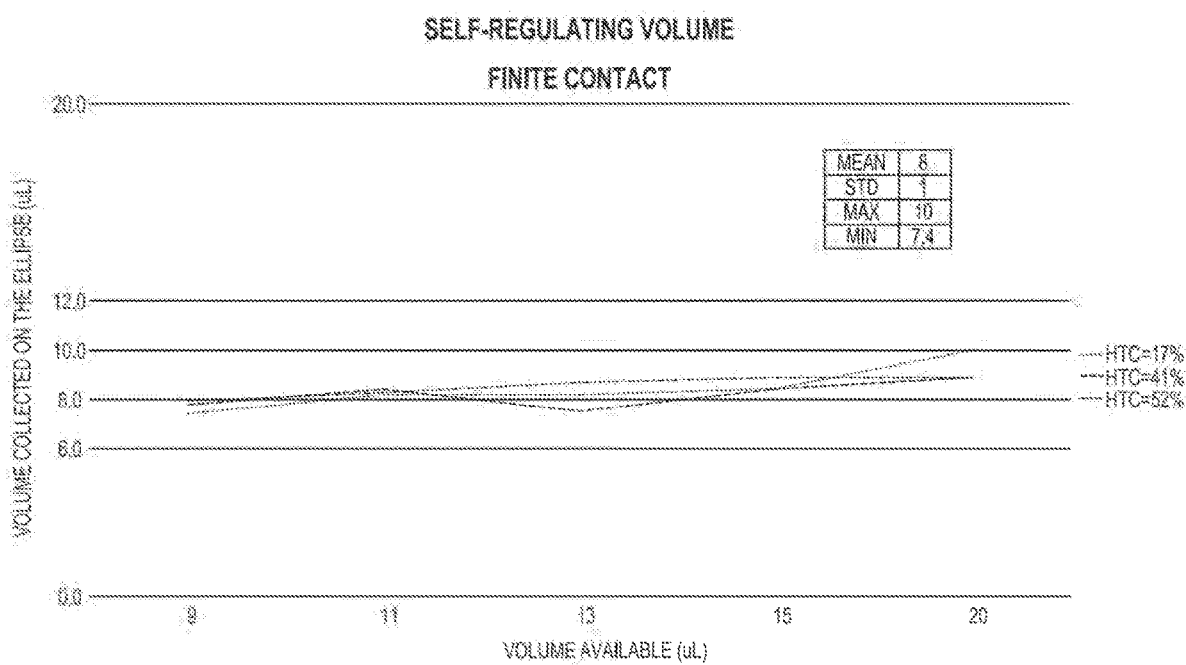
FIG. 11 shows further body fluid volumetric test results obtained using finite contact with blood samples and one embodiment of cartridge 20.

Referring now to FIGS. 10 and 11 there are shown the results of experiments similar to those illustrated in FIGS. 7 and 8, but where the time period over which blood was drawn up into cartridges 20 was shortened. In FIG. 8, 3 blood drops or samples with different concentrations of hematocrit were used, and 5 different volumes of blood were made available to cartridges 20 in each sample. In the tests of FIGS. 7 and 8, cartridges 20 contacted blood drops for prolonged periods of time ("prolonged contact") until blood no longer aspirated onto layer 30. In FIGS. 10 and 11, in contrast, cartridges 20 only contacted blood drops until cartridge tube 32 was filled. This difference blood collection can be important, because cartridge tube 32 can be employed as an additional component in cartridge 20 to regulate the amount of blood volume aspirated onto layer 30 of cartridge 20. Thus, the results illustrated in FIGS. 10 and 11, the volume absorbed by and/or dispersed onto sheet, layer or membrane 30 is more consistent (ranging around 8 uL±1 uL) than that reflected by FIGS. 7 and 8 because blood is drawn from a blood drop until only the volume associated with tube 32 itself is filled or nearly filled. After aspirating the full or near-full volume of tube 32, cartridge 20 is removed from contact with the blood drop or sample, the blood contained in tube 32 is drawn onto paper, layer, sheet, or membrane 30 by capillary action.

FIG. 11 graphically presents the results set forth in the table of FIG. 10. In FIG. 11, a relatively constant "self-regulated volume" behavior of cartridges 20 is illustrated using the "finite contact" method described in connection with FIG. 10, where a blood sample is drawn up into cartridge tube 32 only until tube 32 is filled or nearly-filled, whereupon further aspiration into tube 32 is terminated. The horizontal line shown in FIG. 11 shows that cartridges 20 absorb and disperse onto layer or sheet 30 a constant volume ranging between about 7 uL and about 9 uL on average, regardless of the volume initially available from a blood drop for aspiration (about 9 uL to about 20 uL as tested).

Figure 12A:
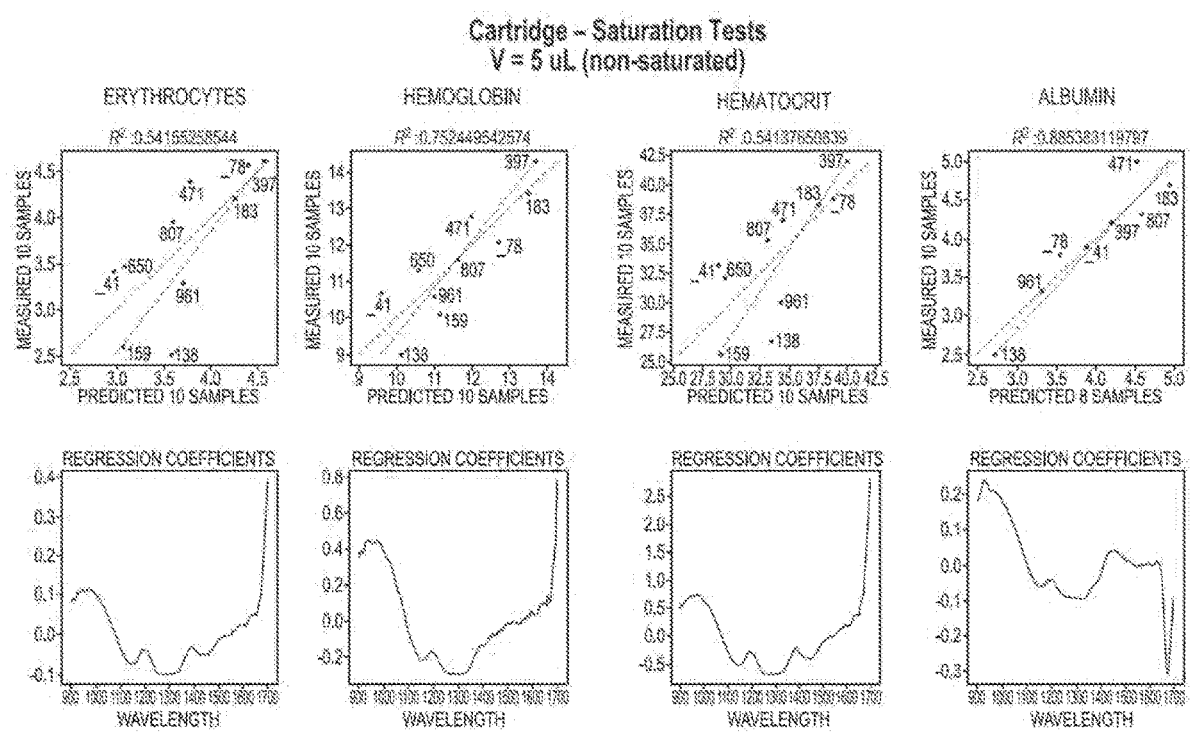
FIG. 12(a) shows predicted results obtained using "non-saturated" paper layer 30 in one embodiment of cartridge 20.
Figure 12B:
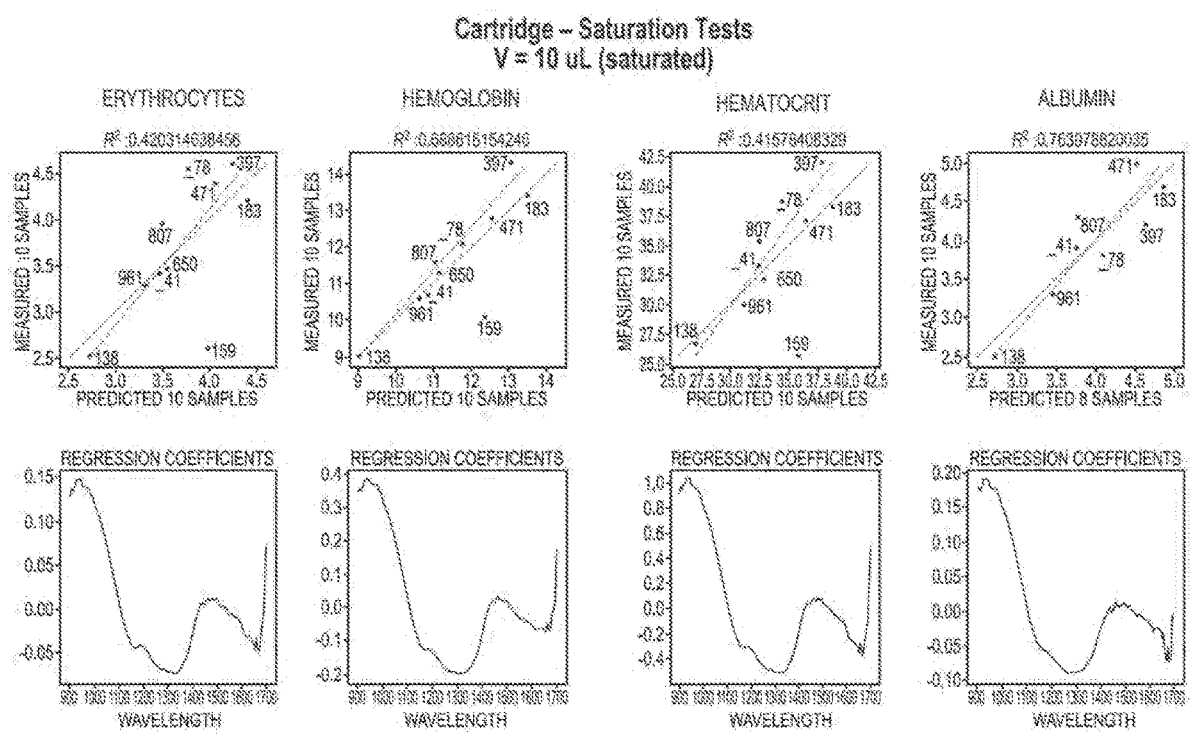
FIG. 12(b) shows predicted results obtained using "saturated" paper layer 30 in one embodiment of cartridge 20.

Referring now to FIGS. 12(a) and 12(b), prediction models for 4 parameters measured in blood samples (erythrocytes-cells, hemoglobin-protein, hematocrit-ratio, albumin-protein) are shown. FIGS. 12(a) and 12(b) illustrate the predicted performance, for the same types of blood samples, acquired in the same types of cartridges 20, but using different volumes, in a "non-saturated" state (FIG. 12(a)) and in a "saturated" state (FIG. 12(b)).

In FIG. 12(a), the results shown reflect the collection of 5 uL volumes of "non-saturated" blood samples onto single paper layers 30 of cartridges 20. The cartridges in FIG. 12(a) are considered "non-saturated" because blood samples were employed to fill, but not entirely fill, paper layer 30. In FIG. 12(b), the results shown reflect the collection of 9 uL volumes of "saturated" blood samples onto single paper layers 30 of cartridges 20. The cartridges in FIG. 12(b) are considered "saturated" because blood samples were employed to fill substantially the entirety of paper layer 30.

Referring now to In FIGS. 12(a) and 12(b), it will be seen that correlation values $R^2$ are lower in FIG. 12(b) than in FIG. 12(a), which demonstrates that cartridges 20 operating in a region of non-saturation promote greater precision in the prediction of the indicated blood parameters. Thus, employing non-saturated samples in cartridges may be important when working in at least the near-infrared spectrum.

As will become apparent to those skilled in the art after having read and understood the specification, drawings and claims of the present patent application, numerous embodiments, additions, permutations, modifications, and combinations of cartridge 20 and its various components, not shown explicitly herein, are contemplated.

According to some embodiments, system 10 is configured to measure in human blood the following parameters: hemoglobin concentration, and erythrocyte, hematocrit and RDW count. As described above, blood samples are preferably collected and homogeneously spread onto at least one sheet, layer or membrane 30 of cartridge 20 for spectroscopic analysis. Light absorbance spectra combined with chemometric methods and algorithms developed for each analyte allow analyte prediction. Near-infrared (NIR) wavelengths employed by spectroscopic device 60 can be, by way of non-limiting example, 900-2500 nm. The present disclosure may also be applied to combined visible light (VIS) and near-infrared NIR measurements (for example, wavelengths of 400-2500 nm). Depending on the specific analyte and biological fluid employed, ultraviolet light (UV) may also be used (for example over wavelengths of 200-2500 nm). Fluorescence results, where desired, may generally be obtained in the UV light spectrum.

In some embodiments, system 10 is portable, non-invasive and capable of producing results that require no operator calibration, interpretation or calculations. As a result, at least some embodiments of system 10 may be applied in point-of-care settings as described above, such as at-home, in a physician's or nurse's office, in a pharmacy, etc.

One of the problems addressed by some embodiments of system 10 concerns the quantification of key parameters in medical diagnosis by counting cells and measuring the concentration of hemoglobin in a given volume of blood. These analyses are currently performed by expensive, high-volume equipment that works with a minimum sample volume of for example 175 µL, thus requiring an invasive venipuncture collection procedure to collect the sample. Because such equipment is fixed and stationary, it must be employed in a laboratory setting, and requires qualified health professionals to operate the machine.

Some embodiments of system 10, in contrast, are portable or semi-portable. Spectroscopic device 60 can be portable or semi-portable, and cartridges 20 are portable and disposable. According to some embodiments, system 10 does not require reagents or consumables, and in addition to other capabilities described above, is configured to analyze cellular components of the blood as well as metabolites thereof. The body fluid sample volume required by system 10 does not exceed 40 µL, preferably does not exceed 30 µl, and even more preferably does not exceed 20 µl. Such a volume can preferably be reduced to 10 µL by using different alpha layers of the cartridge, as explained in further detail below, which facilitates body fluid sample collection via finger prick.

System 10 may also be employed in the context of venous blood-plasma samples and capillary blood samples. The procedure for analysis requires the placement of the blood sample 12 in cartridge 20 with a short waiting period so that the sample 12 can completely spread across membrane, layer or sheet 30. This waiting period should not exceed 60 seconds. The waiting period is preferably in a time range between 30 and 60 seconds. Time is a fixed variable, and in some embodiments it may be important for system performance and accuracy that the waiting period not exceed 60, 120, or 180 seconds.

Later, and in one embodiment, a user can seal cartridge 20 with an optically transparent layer. Then, cartridge 20 is placed in a suitable NIR support or cartridge docking mechanism 62 for near-infrared or other spectroscopic analysis. In some embodiments, system 10 does not require user intervention during the spectroscopic measurement and analysis steps, and produces nearly-real-time, automatic results that may not require further interpretation or calculations.

Results generated by one embodiment of system 10 were validated against gold standard technology and proven to be an effective and alternative method, particularly with respect to the Siemens ADVIA 120 Hematology System. As described above, and in some selected embodiments, system 10 comprises 3 principal or main elements: an NIR spectrometer 60, a sampling cartridge 20, and software (or an algorithm) loaded in computing device or phone 70 that is configured to process data generated by spectroscopic device 60.

In one embodiment, and as described above, NIR spectrometer 60 is a high precision portable spectrometer which operates with the benefit of digital light processing (DLP) technology, and preferably works according to a light reflectance setup that includes two broadband tungsten lamps to properly illuminate the body fluid sample 12 on sheet, layer or membrane 30, and an input slit, collimating and focusing lenses that collect the optical information in the wavelength range from 900 nm to 1700 nm (see FIG. 5). During a scan, sample 12 is placed against sensor window or aperture 66 and absorbs specific portions and wavelengths of NIR light, and diffusely reflects the non-absorbed light into the collection lens (see FIG. 5). The amount of light that is absorbed at each wavelength is dependent on the molecular makeup of the sample and is specific for each material, which constitutes a chemical fingerprint. For accurate and reliable sensor performance, and as described above, sample cartridge 20 is preferably placed directly against and/or registered accurately with respect to sapphire window or aperture 66 of spectrometer 60. Unwanted physical shifts of cartridge position can lead to improper or low illumination, and in consequence, low reflectance of non-absorbed light can generate erratic or poor measurements and results.

In one embodiment, layer, sheet or membrane 30 of cartridge 20 is a multilayer paper-based component, which is configured to enable homogeneous dispersion of body fluids thereon and therein, and in addition to other capabilities described above, is configured to permit an accurate classification and quantification of biochemical parameters of different cellular blood components and/or biochemical metabolites thereof using an NIR spectrometer. Cartridge 20, as described above, is disposable and displays mechanical, chemical and optical properties that allow blood or body fluid samples to uniformly spread and disperse through or onto layer, sheet or membrane 30 thereof to permit an accurate reading by spectrometer 60.

In one embodiment, at least one layer, sheet or membrane 30 cartridge comprises five different layers:
  Layer alpha: a paper-based layer, wherein at least two types of paper are applied. Further details are described below.
  Layer beta: an element that homogeneously reflects preferably at least 95% of NIR radiation, free of reagents, inert to the sample;
  Layer gamma: a highly stable and compact support that allows reproducibility of the cartridge and thus assures precision of the obtained results;
  Layer delta: a hydrophobic and protective layer to confine the sample into a specific area, which has an opening which contributes to confining the sample to a small area below the said opening, such that the sample will form a highly homogenous distribution in the specific measurement area;
  Layer omega: a highly transmissive in the spectrometer's spectrum, optically clear layer to protect the cartridge and avoid moisture and contamination.

Additionally, cartridge 20 can be renewed or recycled by applying a suitable analyte(s) of interest thereto. This means that the definition of the layers and its architecture can depend on the type of fluid that is to be analyzed.

In one embodiment, software or algorithm refers to a data processing module. This module preferably has several sub-processes such as the following: save the recorded spectrum in a file, preprocess the file, process the spectrum with methods of spectral normalization and correlate for parameter quantification, preferably applying methods of variable selection and dimensionality reduction. The correlation methods may be performed using multivariate regression, such as Partial Least Squares (PLS) or Support Vector Machines (SVM), or machine-learning techniques like random decision forests. The final process exports the result value for each parameter.

Homogeneity of body fluid dispersion on layer, sheet or membrane 30 is important, as a typical sensor imaging area is rather substantial and thus lack of homogeneity in the sensor area can be a source of error. Also, the overall reflectance of cartridge 20, mostly given by the combination of the paper-based alpha layer and the reflecting beta layer, is relevant for obtaining precise results. Also, results have been found to be highly dependent on the physical stability of the assembled cartridge which is provided by a support gamma layer, ensuring that even as the liquid sample infuses the assembly, there is no appreciable bending, warping or curling of the assembly layers.

Further details regarding some embodiments are to be found in the '8719 European patent application, the entirety of which is incorporated by reference herein as described above.

In another embodiment, there is provided a method of spectroscopically analyzing a mammalian body fluid sample contained in a cartridge configured for use in conjunction with a corresponding spectroscopic mammalian body fluid analysis device, the spectroscopic device comprising at least one light source, at least one reflected light sensor, and at least one light transmission and light acquisition aperture, the cartridge comprising a cartridge frame or body and a cartridge opening or window disposed in the frame or body, the opening or window sized and shaped to operate in conjunction with the at least one light source, the at least one reflected light sensor, and the at least one aperture of the spectroscopic device, at least body fluid dispersing sheet, layer or membrane being disposed in or across at least portions of the cartridge opening or window, a body fluid sample capillary tube or channel being formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body, wherein the opening or window, the at least one body fluid dispersing sheet, layer or membrane, and the body fluid sample capillary tube or channel are together configured to deliver and disperse a predetermined or near-predetermined amount or volume of a body fluid sample taken from a mammal and introduced to the tube or channel inlet at least one of onto, into, through and across the at least one body fluid dispersing sheet, layer or membrane for subsequent analysis of the body fluid sample by the corresponding spectroscopic device when the cartridge is placed or fitted in an operative position or location with respect to the corresponding spectroscopic device, the method comprising obtaining or acquiring the body fluid sample; placing the tube or channel inlet of the cartridge in, on, or near the body fluid sample such that the predetermined amount or volume of the body fluid sample is delivered and dispersed at least one of onto, into, through and across the at least one dispersing sheet, layer or membrane; placing the cartridge in an operative position with respect to the corresponding spectroscopic device, and analyzing the body fluid sample contained in the cartridge with the corresponding spectroscopic device.

Such an embodiment may further comprise one or more of: (a) the spectroscopic device being a fluorescence spectrometer or being configured to perform one or more of near-infrared spectroscopy, infrared spectroscopy, ultraviolet spectroscopy, visible light spectroscopy, mass spectroscopy, and fluorescent spectropscopy on the body fluid sample in the cartridge; (b) the body fluid sample comprising human or animal blood, and the analysis further comprises one or more of determining amounts, percentages, volumes or predictions of one or more of levels of oxygen, nutrients, waste, electrolytes, glucose, urea, total proteins, proteins, albumins, triglycerides, hematocrits, hemoglobins, complete blood count, circulating tumor cells, tumor markers, CA 15.3 markers, TRU-QUANT and CA 27.29 markers, CA125 markers, CEA (carcinoembryonic antigen) markers, viruses, and pathologies associated with, contained in, or detectable in the body fluid sample; (c) further comprising augmenting or adding augmented one or more of a liquid buffer, a reagent, a fluid viscosity alteration agent, and a solvent to the body fluid sample; (d) the body fluid sample comprising a human body fluid, and the analysis further comprises one or more of determining characteristics of the body fluid sample for forensic or criminal investigation purposes; (e) the cartridge and spectroscopic device being together configured, shaped and sized for use in at least one of at-home patient, clinical, medical office, and outpatient settings or applications; (f) after the body fluid sample has been dispersed onto the at least one sheet, layer or membrane, the body fluid sample becoming a dried fluid spot sample on the at least one sheet, layer or membrane; (g) the dried fluid spot sample being one of a dried blood spot (DBS), dried urine spot (DUS) and a dried saliva spot (DSS); (h) the predetermined amount or volume of the body fluid drawn onto the at least one dispersing sheet, layer or membrane ranging between about 3 µl and about 10 µl; (i) the predetermined amount or volume of the body fluid sample drawn onto the at least one dispersing sheet, layer or membrane ranging between about 2 µl and about 14 µl; (j) the predetermined amount or volume of the body fluid sample drawn onto the at least one dispersing sheet, layer or membrane ranging between about 2 µl and about 20 µl; (k) the predetermined amount or volume of the body fluid sample drawn onto the at least one dispersing sheet, layer or membrane being substantially evenly distributed and dispersed across the at least one sheet, layer or membrane; (l) the predetermined amount or volume of the body fluid sample drawn onto the at least one dispersing sheet, layer or membrane not completely saturating the at least one sheet, layer or membrane; (m) further comprising pricking a skin or a finger of a human patient or animal, or performing a venipuncture, to acquire the body fluid sample; (n) the at least one dispersing sheet, layer or membrane comprising one or more of paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly(vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly (vinylidene fluoride), polyester, polycarbonate, cellulose acetate, cellulose nitrate, poly(vinyl chloride), and nylon; (o) the sheet, layer or membrane being configured to pull the body fluid sample thereacross or therethrough to near, at or beyond a perimeter of the window or opening; (p) the outlet of the tube or channel being disposed in a central or near-central bottom portion of the opening or window such that the body fluid sample is dispersed initially from a location near or adjoining a center of the at least one sheet, layer or membrane; (q) the outlet of the tube or channel being located inside a perimeter of the window or opening and points towards or is located near or at a central or near-central bottom portion of the opening or window; (r) the sheet, layer or membrane being located above a bottom, side or sidewall surface of the opening or window, and the outlet of the tube or channel is disposed near or on the bottom surface of the window or opening, such that air and body fluid flow through the tube or channel into the opening and onto the sheet, layer or membrane is facilitated; (s) the spectroscopic device being a fluorescence spectrometer or being configured to operate in one or more of an infrared light spectrum, a near-infrared light spectrum, a visible light spectrum, and an ultraviolet light spectrum; (t) the cartridge and the spectroscopic device being together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device; (u) the tube or channel inlet comprising a material or coating having a low contact angle as regards the body fluid; (v) (u) the tube or channel outlet comprising a material or coating having a low contact angle as regards the body fluid; (w) prior to introduction of the body fluid sample thereto, no reactive or body fluid contaminating materials, chemicals, additives or constituents being disposed in or on the cartridge or selected portions thereof; (x) the at least one dispersing sheet, layer or membrane comprising a material exhibiting a low spectral absorbance; (y) the cartridge being configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device; (z) the cartridge comprising a grippable or matingly engageable structural feature or element disposed on a portion thereof, the structural feature or element being configured to facilitate human or machine handling of the cartridge; (aa) further comprising sealing or capping at least portions of the cartridge to prevent contamination of the body fluid sample disposed therein; (bb) further comprising providing a machine-readable label or unique identifier having information regarding the body fluid sample disposed in the cartridge; (cc) further comprising providing the cartridge to a laboratory for wet or chemical analysis of the body fluid sample; (dd) the cartridge being configured and shaped for use with a corresponding wet analysis tube or receptacle; (ee) the cartridge being configured and shaped to permit the at least one sheet, layer or membrane to be cut or removed from the cartridge and extracted therefrom; and (ff) the body fluid sample contained in the cartridge being analyzed by the corresponding spectroscopic device within a time period of one or more of less than about 120 seconds, less than about 60 seconds, less than about 45 seconds, less than about 30 seconds, and less than about 15 seconds after the body fluid sample has been drawn into the cartridge.

In yet another embodiment, there is provided a system for spectroscopically analyzing a mammalian body fluid sample, the system comprising a spectroscopic body fluid analysis device, the device comprising at least one light source, at least one reflected light sensor, and the at least one light transmission and light acquisition aperture, at least one corresponding cartridge configured for use in conjunction with the spectroscopic body fluid analysis device, the cartridge comprising a cartridge frame or body, a cartridge opening or window disposed in the frame or body, the opening or window being sized and shaped to operate in conjunction with the at least one light source, the at least one reflected light sensor, and the at least one aperture of the spectroscopic device, at least one body fluid dispersing sheet, layer or membrane being disposed in or across at least portions of the cartridge opening or window, and a body fluid sample capillary tube or channel formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body; wherein the opening or window, the at least one body fluid dispersing sheet, layer or membrane, and the body fluid sample capillary tube or channel are together configured to deliver and disperse a predetermined amount or volume of a body fluid sample taken from a mammal and introduced to the tube or channel inlet at least one of onto, into, through and across the at least one body fluid dispersing sheet, layer or membrane for subsequent analysis of the body fluid sample by the spectroscopic device when the corresponding cartridge is placed or fitted in an operative position or location with respect to the spectroscopic device.

Such an embodiment may further comprise one or more of: (a) the body fluid sample being augmented by one or more of a liquid buffer, a reagent, a fluid viscosity alteration agent, and a solvent; (b) the cartridge and spectroscopic device are together configured, shaped and sized for use in at least one of at-home patient, clinical, medical office, and outpatient settings or applications; (c) the predetermined amount or volume of the body fluid sample drawn onto the at least one dispersing sheet, layer or membrane ranging between about 3 µl and about 10 µl; (d) the predetermined amount or volume of the body fluid sample drawn onto the at least one dispersing sheet, layer or membrane ranging between about 2 µl and about 14 µl; (e) the predetermined amount or volume of the body fluid sample being acquired from a pool of bodily fluid taken from the mammal that ranges between about 2 µl and about 20 µl; (f) the predetermined amount or volume of the body fluid sample drawn onto the at least one dispersing sheet, layer or membrane being substantially evenly distributed and dispersed across the at least one sheet, layer or membrane; (g) the predetermined amount or volume of the body fluid sample drawn onto the at least one dispersing sheet, layer or membrane not completely saturating the at least one sheet, layer or membrane; (h) the body fluid sample comprising human blood acquired by a skin or finger prick or through venipuncture of a patient; (i) the spectroscopic device being a fluorescence spectrometer or being configured to operate in one or more of an infrared light spectrum, a near-infrared light spectrum, a visible light spectrum, and an ultraviolet light spectrum; (j) the cartridge and the spectroscopic device being together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device; (k) at least one of the tube or channel and frame or body comprising a polymer, a plastic and a polymeric material; (l) the polymer or plastic of the at least one of the tube or channel or frame or body is at least one of anticoagulant-free, heparin-free, and comprises a polylactic acid (PLA) bioplastic; (m) the cartridge being configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device; (n) further comprising a cap, container or bag configured to seal at least portions of the cartridge to prevent contamination of the body fluid sample disposed therein; (o) further comprising or having associated therewith a machine-readable label or unique identifier comprising or providing access to information regarding the body fluid sample disposed in the cartridge; (p) the cartridge being sized, shaped and configured for handling, processing, and analysis of the body fluid sample in a laboratory; (q) the cartridge being configured and shaped for use with a corresponding wet or chemical analysis tube or receptacle; and (r) the cartridge being configured and shaped to permit the at least one sheet, layer or membrane to be cut or removed from the cartridge and extracted therefrom.

The foregoing and other aspects, features, advantages, and characteristics of systems, devices, components and methods associated with a body fluid analysis system, which, according to some embodiments, can be employed in at-home, clinical, medical office and outpatient settings and applications. As shown. the system can be configured to provide results within a short period of time after a body fluid sample has been acquired from a patient such as by a finger or skin prick.

In some embodiments, and as described in detail above, a body fluid sample cartridge is configured for use in conjunction with a corresponding spectroscopic body fluid analysis device, where the cartridge comprises one or more body fluid dispersing sheets, layers or membranes. In some embodiments, the cartridge is configured to deliver and disperse a predetermined amount or volume of a body fluid sample taken from a human or animal onto, into, through or across the body fluid dispersing sheet, layer or membrane disposed within the cartridge for subsequent analysis of the body fluid sample by a corresponding spectroscopic device.

The system and the cartridge associated therewith can be configured to eliminate numerous bottlenecks, inefficiencies, and high costs associated with conventional body fluid analysis techniques currently employed in the medical field, and can be configured to provide useful results rapidly. Subsequent chemical or wet analysis of the acquired body fluid sample in a laboratory can also be carried out using the cartridge containing the sample.

Various embodiments of body fluid cartridges, spectroscopic devices, and computing devices and techniques beyond those described and disclosed explicitly herein are contemplated, including, but not limited to, cartridges that are not formed of plastics or polymers, cartridges that contain 1, 2, 3, 4, 5, 6, 7 or more layers, sheets, or membranes, cartridges that comprise multiple tubes or channels for drawing body fluids up into cartridge 20, and cartridges that are configured and shaped for use in wet chemical or non-spectroscopic applications and analysis.

After having read and understood the specification, drawings and claims presented herein, it will become apparent to those skilled in the art that important problems existing in the prior art are solved by the various embodiments described and disclosed herein. Such problems include, but are not limited to: (a) medical practice being reactive and based on episodical information presented by patients, mostly through an expensive and timely process that ends up with short physical meetings in a medical practice; (b) follow-up and prevention are difficult because there is no data rich continued feedback loop, and doctors cannot manage what they do not see and patients cannot act on what they cannot measure; (c) point-of-care testing is generally performed outside clinical practice; (d) sample pathological parameters are unknown upon arrival at a lab, and long turn-around times to provide lab results can occur; and (e) blood sampling often requires a health care professional to draw blood (e.g., vein puncture).

The various embodiments described and disclosed herein permit different approaches to acquiring and processing body fluid samples, including, but not limited to: (a) enabling the healthcare paradigm to shift from reactive to proactive; (b) bringing laboratory accuracy to the point of care and point of need; (c) simplifying blood or body fluid testing and making it accessible anywhere to anyone; (d) on the spot results and continued health status monitoring; (e) high levels of expertise are not required to obtain and process body fluid samples, and the samples can be acquired in almost any setting; and (f) minimally invasive body fluid sampling methods can be employed.

The various embodiments described and disclosed herein also permit different solutions to existing problems to be provided, including, but not limited to: (a) predictive intelligence about health and wellness of a patient can be provided by combining body fluid microsampling, spectroscopy, and bio-informatics and learning algorithms techniques in a cloud-connected platform that configured to detect and analyze one or more biomarkers; (b) miniature, mobile and simple-to-use systems for body fluid and blood testing can be provided, which in some embodiments require only a self-collected single drop of blood or other body fluid and a single-use disposable cartridge; multiple tests can be performed using a single drop of blood or other body fluid; (c) results can be visualized by the user/patient and transmitted to a health care professional, permitting a longitudinal database to be built, and accurate prediction of health status and disease to be provided; (d) employing non-destructive analytical techniques, which permit the same sample (or cartridge) to be sent to a laboratory for further analysis; the fact that the lab can receive upfront already processed pathological data significantly streamlines the subsequent lab analysis that is to be performed.

What have been described above are examples and embodiments of the systems, devices, components and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are contemplated and possible.

Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of cartridges 20 will fall within the scope of the various embodiments. Those skilled in the art should appreciate that they may readily use the present disclosure as a basis for designing or modifying other devices, structures, materials, components, hardware, software, methods, techniques, and/or processes, for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, not only in performing analyses of human blood, but also in performing rapid and cost-effective analyses of many different types of body fluids from human and animal subjects.

We claim:

1. A body fluid sample cartridge configured for use in conjunction with a corresponding spectroscopic body fluid analysis device, the spectroscopic device comprising at least one light source, at least one reflected light sensor, and at least one light transmission and light acquisition aperture, the cartridge comprising:

a cartridge frame or body;

an uncovered cartridge opening disposed in the frame or body, the opening being sized and shaped to operate in cooperation and in conjunction with the at least one light source, the at least one reflected light sensor, and the at least one aperture of the spectroscopic device;

at least one body fluid dispersing sheet, layer or membrane disposed in, across or near at least portions of the cartridge opening such that at least portions of the sheet, layer or membrane are spaced apart from and not in contact with the cartridge frame or body, and at least one body fluid sample capillary tube or channel formed or situated in or on a portion of the cartridge frame or body, the tube or channel comprising a body fluid collection inlet disposed adjacent to an exterior portion of the frame or body and a body fluid dispersion outlet disposed adjacent to a portion of the opening in the frame or body;

wherein the uncovered cartridge opening, the tube or channel, and the sheet, layer or membrane are together configured to acquire, deliver and disperse through capillary action a predetermined amount or volume of a body fluid sample from a patient that is introduced to the body fluid collection inlet and delivered through the tube or channel and the body fluid dispersion outlet thereof at least one of onto, into, through and across the sheet, layer or membrane, and further wherein the uncovered cartridge opening, the tube or channel, and the sheet, layer or membrane are together configured to facilitate a flow of air and the body fluid sample through the tube or channel into the opening and onto the sheet, layer or membrane, and the body fluid sample on the sheet, layer or membrane is configured to be analyzed by the corresponding spectroscopic device when the cartridge is placed or fitted in an operative position or location with respect thereto in the corresponding spectroscopic device.

2. The body fluid sample cartridge of claim 1, wherein the predetermined amount or volume of the body fluid sample is substantially evenly distributed and dispersed across or over the at least one sheet, layer or membrane.

3. The body fluid sample cartridge of claim 1, wherein the body fluid sample becomes a dried fluid spot sample on the at least one sheet, layer or membrane.

4. The body fluid sample cartridge of claim 3, wherein the dried fluid spot sample is one of a dried blood spot (DBS), dried urine spot (DUS) and a dried saliva spot (DSS).

5. The body fluid sample cartridge of claim 1, wherein the tube or channel and the sheet, layer or membrane are disposed substantially in a same plane in the cartridge.

6. The body fluid sample cartridge of claim 1, wherein the body fluid sample comprises one or more of blood, menstrual blood, urine, saliva, semen, vaginal fluid, and sweat.

7. The body fluid sample cartridge of claim 1, wherein the body fluid sample is augmented by one or more of a liquid buffer, a reagent, a fluid viscosity alteration agent, and a solvent.

8. The body fluid sample cartridge of claim 1, wherein the cartridge and spectroscopic device are together configured, shaped and sized for use in at least one of at-home patient, clinical, medical office, and outpatient settings or applications.

9. The body fluid sample cartridge of claim 1, wherein the predetermined amount or volume of the body fluid sample drawn onto the at least one dispersing sheet, layer or membrane ranges between about 3 µl and about 10 µl.

10. The body fluid sample cartridge of claim 1, wherein the predetermined amount or volume of the body fluid sample drawn onto the at least one dispersing sheet, layer or membrane ranges between about 2 µl and about 14 µl.

11. The body fluid sample cartridge of claim 1, wherein the predetermined amount or volume of the body fluid sample is acquired from a pool of bodily fluid taken from the patient that ranges between about 2 µl and about 20 µl.

12. The body fluid sample cartridge of claim 1, wherein the predetermined amount or volume of the body fluid sample drawn onto the at least one dispersing sheet, layer or membrane does not completely saturate the at least one sheet, layer or membrane.

13. The body fluid sample cartridge of claim 1, wherein the at least one dispersing sheet, layer or membrane is absorbent.

14. The body fluid sample cartridge of claim 1, wherein the body fluid sample comprises human blood acquired by a skin or finger prick or through venipuncture of the patient.

15. The body fluid sample cartridge of claim 1, wherein the opening has a minimum width or diameter ranging between about 2 mm and about 8 mm, has a maximum width or diameter ranging between about 3 mm and about 20 mm, and has a sidewall height or depth to a bottom surface thereof ranging between about 0.25 mm and about 3 mm.

16. The body fluid sample cartridge of claim 1, wherein the tube or channel has a diameter ranging between about 0.25 mm and about 2.0 mm or a diameter ranging between about 0.5 mm and about 1.5 mm.

17. The body fluid sample cartridge of claim 1, wherein a surface area within the opening of the at least one dispersing sheet, layer or membrane ranges between about 10 $mm^2$ and about 60 $mm^2$.

18. The body fluid sample cartridge of claim 1, wherein the at least one dispersing sheet, layer or membrane comprises one or more of paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly (vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly(vinylidene fluoride), polyester, polycarbonate, cellulose acetate, cellulose nitrate, poly(vinyl chloride), and nylon.

19. The body fluid sample cartridge of claim 1, wherein the sheet, layer or membrane is configured to pull the body fluid sample thereacross or therethrough to near, at or beyond a perimeter of the opening.

20. The body fluid sample cartridge of claim 1, wherein the outlet of the tube or channel is disposed in a central or near-central portion of the opening such that the body fluid sample is dispersed initially from a location near or adjoining a center of the at least one sheet, layer or membrane.

21. The body fluid sample cartridge of claim 1, wherein the outlet of the tube or channel is located inside a perimeter of the opening and points towards or is located near or at a central or near-central bottom portion of the opening.

22. The body fluid sample cartridge of claim 1, wherein the spectroscopic device is a spectrometer configured to operate in one or more of an infrared light spectrum, a near-infrared light spectrum, a visible light spectrum, and an ultraviolet light spectrum.

23. The body fluid sample cartridge of claim 1, wherein the cartridge and the spectroscopic device are together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device.

24. The body fluid sample cartridge of claim 1, wherein the body fluid sample comprises blood, and the analysis further comprises one or more of determining amounts, percentages, volumes or predictions of one or more of levels of oxygen, nutrients, waste, electrolytes, glucose, urea, total proteins, bacteria, proteins, albumins, triglycerides, hematocrits, hemoglobins, complete blood count, circulating tumor cells, tumor markers CA 15.3 markers, TRU-QUANT and CA 27.29 markers, CA 125 markers, CEA (carbinoembryonic antigen) markers, viruses, and pathologies associated with, contained in, or detectable in the body fluid sample.

25. The body fluid sample cartridge of claim 1, wherein at least one of the channel and frame or body comprises a polymer, a plastic and a polymeric material.

26. The body fluid sample cartridge of claim 25, wherein polymer or plastic is at least one of anticoagulant-free, heparin-free, and comprises a polylactic acid (PLA) bioplastic.

27. The body fluid sample cartridge of claim 1, wherein the tube or channel inlet comprises a convex shape to facilitate capillary uptake of the body fluid into the cartridge.

28. The body fluid sample cartridge of claim 1, wherein the tube or channel inlet comprises a material characterized by a low contact angle thereby to facilitate capillary uptake of the body fluid into the cartridge.

29. The body fluid sample cartridge of claim 1, wherein, prior to introduction of the body fluid sample to the at least one sheet, layer or membrane, no reactive or body fluid contaminating materials, chemicals, additives or constituents are disposed in or on the cartridge or selected portions thereof.

30. The body fluid sample cartridge of claim 1, wherein the at least one dispersing sheet, layer or membrane comprises a material exhibiting a low spectral absorbance.

31. The body fluid sample cartridge of claim 1, wherein the cartridge is configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device.

32. The body fluid sample cartridge of claim 1, wherein the opening is at least one of elliptical in shape, circular in shape, rectangular in shape, square in shape, triangular in shape, and non-circular in shape.

33. The body fluid sample cartridge of claim 1, wherein the cartridge comprises a grippable or matingly engageable structural feature or element disposed on a portion thereof, the structural feature or element being configured to facilitate human or machine handling of the cartridge.

34. The body fluid sample cartridge of claim 1, further comprising a cap, container or bag configured to seal at least portions of the cartridge to prevent contamination of the body fluid sample disposed therein.

35. The body fluid sample cartridge of claim 1, further comprising or having associated therewith a machine-readable label or unique identifier comprising or providing access to information regarding the body fluid sample disposed in the cartridge.

36. The body fluid sample cartridge of claim 1, wherein the cartridge is sized, shaped and configured for handling, processing, and analysis of the body fluid sample in a laboratory.

37. The body fluid sample cartridge of claim 1, wherein the cartridge is configured and shaped for use with a corresponding wet or chemical analysis tube or receptacle.

38. The body fluid sample cartridge of claim 1, wherein the cartridge is configured and shaped to permit the at least one sheet, layer or membrane to be cut or removed from the cartridge and extracted therefrom.

39. A method of spectroscopically analyzing a body fluid sample from a patient, the body fluid sample being contained in a cartridge configured for use in conjunction with a corresponding spectroscopic body fluid analysis device, the spectroscopic device comprising at least one light source, at least one reflected light sensor, and at least one light transmission and light acquisition aperture, the cartridge comprising a cartridge frame or body, an uncovered cartridge opening disposed in the frame or body, the opening being sized and shaped to operate in cooperation and in conjunction with the at least one light source, the at least one reflected light sensor, and the at least one aperture of the spectroscopic device, at least one body fluid dispersing sheet, layer or membrane being disposed in, across or near at least portions of the cartridge opening such that at least portions of the sheet, layer or membrane are spaced apart from and not in contact with the cartridge frame or body, and at least one body fluid sample capillary tube or channel is formed or situated in or on a portion of the cartridge frame or body, the tube or channel comprising a body fluid collection inlet disposed adjacent to an exterior portion of the frame or body and a body fluid dispersion outlet disposed adjacent to a portion of the opening in the frame or body, wherein the uncovered cartridge opening, the tube or channel, and the sheet, layer or membrane are together configured to acquire, deliver and disperse through capillary action a predetermined amount or volume of a body fluid sample from the patient that is introduced to the body fluid collection inlet and delivered through the tube or channel and the body fluid dispersion outlet thereof at least one of onto, into, through and across the sheet, layer or membrane, and further wherein the uncovered cartridge opening, the tube or channel, and the sheet, layer or membrane are together configured to facilitate a flow of air and the body fluid sample through the tube or channel into the opening and onto the sheet, layer or membrane, and the body fluid sample on the sheet, layer or membrane is configured to be analyzed by the corresponding spectroscopic device when the cartridge is placed or fitted in an operative position or location with respect thereto in the corresponding spectroscopic device, the method comprising:

obtaining or acquiring the body fluid sample;
 placing the tube or channel inlet of the cartridge in, on, or near the body fluid sample such that the predetermined amount or volume of the body fluid sample is acquired, delivered and dispersed at least one of onto, into, through and across the at least one dispersing sheet, layer or membrane;
 placing the cartridge in an operative position with respect to the corresponding spectroscopic device, and
 analyzing the body fluid sample contained in the cartridge with the corresponding spectroscopic device.

40. The method of claim 39, wherein the predetermined amount or volume of the body fluid sample is substantially evenly distributed and dispersed across or over the at least one sheet, layer or membrane.

41. The method of claim 39, wherein the body fluid sample becomes a dried fluid spot sample on the at least one sheet, layer or membrane.

42. The method of claim 41, wherein the dried fluid spot sample is one of a dried blood spot (DBS), dried urine spot (DUS) and a dried saliva spot (DSS).

43. The method of claim 39, wherein the tube or channel and the sheet, layer or membrane are disposed substantially in a same plane in the cartridge.

44. The method of claim 39, wherein the spectroscopic device is a spectrometer configured to perform one or more of near-infrared spectroscopy, infrared spectroscopy, ultraviolet spectroscopy, and visible light spectroscopy on the body fluid sample in the cartridge.

45. The method of claim 39, wherein the body fluid sample comprises blood, and the analysis further comprises one or more of determining amounts, percentages, volumes or predictions of one or more of levels of oxygen, nutrients, waste, electrolytes, glucose, urea, total proteins, bacteria, proteins, albumins, triglycerides, hematocrits, hemoglobins, complete blood count, circulating tumor cells, tumor markers, CA 15.3 markers, TRU-QUANT and CA 27.29 markers, CA125 marker, CEA (carbino-embryonic antigen) markers, viruses, and pathologies associated with, contained in, or detectable in the body fluid sample.

46. The method of claim 39, further comprising augmenting or adding one or more of a liquid buffer, a reagent, a fluid viscosity alteration agent, and a solvent to the body fluid sample.

47. The method of claim 39, wherein the body fluid sample comprises a human body fluid, and the analysis further comprises one or more of determining characteristics of the body fluid sample for forensic or criminal investigation purposes.

48. The method of claim 39, wherein the cartridge and spectroscopic device are together configured, shaped and sized for use in at least one of at-home patient, clinical, medical office, and outpatient settings or applications.

49. The method of claim 39, wherein the predetermined amount or volume of the body fluid sample drawn onto the at least one dispersing sheet, layer or membrane ranges between about 3 μl and about 10 μl.

50. The method of claim 39, wherein the predetermined amount or volume of the body fluid sample drawn onto the at least one dispersing sheet, layer or membrane ranges between about 2 μl and about 14 μl.

51. The method of claim 39, wherein the predetermined amount or volume of the body fluid sample drawn onto the at least one dispersing sheet, layer or membrane ranges between about 2 μl and about 20 μl microliters.

52. The method of claim 39, wherein the predetermined amount or volume of the body fluid sample drawn onto the at least one dispersing sheet, layer or membrane does not completely saturate the at least one sheet, layer or membrane.

53. The method of claim 39, further comprising pricking a skin or a finger of a human patient or animal, or performing a venipuncture, to acquire the body fluid sample.

54. The method of claim 39, wherein the at least one dispersing sheet, layer or membrane comprises one or more of paper, cellulose, a nonwoven polymeric film, fiberglass, spun glass, glass cloth, an inorganic membrane, ceramic, a woven fabric, a knit fabric, a fibrous material, a hydrophilic porous film, nylon-6, nylon-66, poly(vinyl alcohol, a polymer, a polymeric material, a microporous polymer, polytetrafluoroethylene (PTFE), a hydrophobic material, a hydrophilic material, a hydrophobic or hydrophilic microporous polyethylene or polypropylene film, a microporous PTFE film, a microporous hydrophilic film, a microporous material comprising one or more of polyolefin, polyethylene, polypropylene, copoly(ethylene-propylene)), poly(vinylidene fluoride), polyester, polycarbonate, cellulose acetate, cellulose nitrate, poly(vinyl chloride), and nylon.

55. The method of claim 39, wherein the sheet, layer or membrane is configured to pull the body fluid sample thereacross or therethrough to near, at or beyond a perimeter of the opening.

56. The method of claim 39, wherein the outlet of the tube or channel is disposed in a central or near-central bottom portion of the opening such that the body fluid sample is dispersed initially from a location near or adjoining a center of the at least one sheet, layer or membrane.

57. The method of claim 39, wherein the outlet of the tube or channel is located inside a perimeter of the opening and points towards or is located near or at a central or near-central bottom portion of the opening.

58. The method of claim 39, wherein the sheet, layer or membrane is located above a bottom, side or sidewall surface of the opening, and the outlet of the tube or channel is disposed near or on the bottom surface of the opening, such that air and body fluid flow through the tube or channel into the opening and onto the sheet, layer or membrane is facilitated.

59. The method of claim 39, wherein the spectroscopic device is configured to operate in one or more of an infrared light spectrum, a near-infrared light spectrum, a visible light spectrum, and an ultraviolet light spectrum.

60. The method of claim 39, wherein the cartridge and the spectroscopic device are together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device.

61. The method of claim 39, wherein the tube or channel inlet comprises a convex shape to facilitate capillary uptake of the body fluid into the cartridge.

62. The method of claim 39, wherein the tube or channel inlet comprises a material characterized by a low contact angle thereby to facilitate uptake of the body fluid into the cartridge.

63. The method of claim 39, wherein, prior to introduction of the body fluid sample thereto, no reactive or body fluid contaminating materials, chemicals, additives or constituents are disposed in or on the cartridge or selected portions thereof.

64. The method of claim 39, wherein the at least one dispersing sheet, layer or membrane comprises a material exhibiting a low spectral absorbance.

65. The method of claim 39, wherein the cartridge is configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device.

66. The method of claim 39, wherein the cartridge comprises a grippable or matingly engageable structural feature or element disposed on a portion thereof, the structural feature or element being configured to facilitate human or machine handling of the cartridge.

67. The method of claim 39, further comprising sealing or capping at least portions of the cartridge to prevent contamination of the body fluid sample disposed therein.

68. The method of claim 39, further comprising providing a machine-readable label or unique identifier having information regarding the body fluid sample disposed in the cartridge.

69. The method of claim 39, further comprising providing the cartridge to a laboratory for wet or chemical analysis of the body fluid sample.

70. The method of claim 39, wherein the cartridge is configured and shaped for use with a corresponding wet analysis tube or receptacle.

71. The method of claim 39, wherein the cartridge is configured and shaped to permit the at least one sheet, layer or membrane to be cut or removed from the cartridge and extracted therefrom.

72. The method of claim 39, wherein the body fluid sample contained in the cartridge is analyzed by the corresponding spectroscopic device within a time period of one or more of less than about 120 seconds, less than about 60 seconds, less than about 45 seconds, less than about 30 seconds, and less than about 15 seconds after the body fluid sample has been drawn into the cartridge.

73. A system for spectroscopically analyzing a body fluid sample, the system comprising:
a spectroscopic body fluid analysis device, the device comprising at least one light source, at least one reflected light sensor, and the at least one light transmission and light acquisition aperture;
at least one corresponding cartridge configured for use in conjunction with the spectroscopic body fluid analysis device, the cartridge comprising:
a cartridge frame or body;
an uncovered cartridge opening or window disposed in the frame or body, the opening being sized and shaped to operate in cooperation and in conjunction with the at least one light source, the at least one reflected light sensor, and the at least one aperture of the spectroscopic device,
at least one body fluid dispersing sheet, layer or membrane disposed in, across or near at least portions of the cartridge opening such that at least portions of the sheet, layer or membrane are spaced apart from and not in contact with the cartridge frame or body, and
at least one body fluid sample capillary tube or channel formed or situated in or on a portion of the cartridge frame or body, the tube or channel comprising a body fluid collection inlet disposed adjacent to an exterior portion of the frame or body and a body fluid dispersion outlet disposed adjacent to a portion of the opening or window in the frame or body;
wherein the uncovered cartridge opening, the tube or channel, and the sheet, layer or membrane are together configured to acquire, deliver and disperse through capillary actiona predetermined amount or volume of a body fluid sample from a patient that is introduced to the body fluid collection inlet and delivered through the tube or channel and the body fluid dispersion outlet thereof at least one of onto, into, through and across the sheet, layer or membrane, and further wherein the uncovered cartridge opening, the tube or channel, and the sheet, layer or membrane are together configured to facilitate a flow of air and the body fluid sample through the tube or channel into the opening and onto the sheet, layer or membrane, and the body fluid sample on the sheet, layer or membrane is configured to be analyzed by the corresponding spectrosopic device when the cartridge is placed or fitted in an operative position or location with respect thereto in the corresponding spectroscopic device.

74. The system of claim 73, wherein the predetermined amount or volume of the body fluid sample is substantially evenly distributed and dispersed across or over the at least one sheet, layer or membrane.

75. The system of claim 74, wherein the body fluid sample becomes a dried fluid spot sample on the at least one sheet, layer or membrane.

76. The system of claim 75, wherein the dried fluid spot sample is one of a dried blood spot (DBS), dried urine spot (DUS) and a dried saliva spot (DSS).

77. The system of claim 73, wherein the tube or channel and the sheet, layer or membrane are disposed substantially in a same plane in the cartridge.

78. The system of claim 73, wherein the body fluid sample is augmented by one or more of a liquid buffer, a reagent, a fluid viscosity alternation agent, and a solvent.

79. The system of claim 73, wherein the cartridge and spectroscopic device are together configured, shaped and sized for use in at least one of at-home patient, clinical, medical office, and outpatient settings or applications.

80. The system of claim 73, wherein the predetermined amount of volume of the body fluid sample drawn onto the at least one dispersing sheet, layer or membrane ranges between about 3 µl and about 10 µl.

81. The system of claim 73, wherein the predetermined amount or volume of the body fluid sample drawn onto the at least one dispersing sheet, layer or membrane ranges between about 2 µl and about 14 µl.

82. The system of claim 73, wherein the predetermined amount or volume of the body fluid sample is acquired from a pool of bodily fluid taken from the patient that ranges between about 2 µl and about 20 µl.

83. The system of claim 73, wherein the predetermined amount or volume of the body fluid sample drawn onto the at least one dispersing sheet, layer or membrane does not completely saturate the at least one sheet, layer or membrane.

84. The system of claim 73, wherein the body fluid sample comprises blood acquired by a skin or finger prick or through venipuncture of the patient.

85. The system of claim 73, wherein the spectroscopic device is configured to operate in one or more of an infrared light spectrum, a near-infrared light spectrum, a visible light spectrum, and an ultraviolet light spectrum.

86. The system of claim 73, wherein the cartridge and the spectroscopic device are together configured such that the cartridge is configured and shaped to permit reproducible and accurate registration and location of the sheet, layer or membrane with respect to one or more incoming light beams emitted by, and one or more outgoing light beams reflected from the sheet, layer or membrane and detected by, the spectroscopic device.

87. The system of claim 73, wherein the body fluid sample comprises blood, and the analysis further comprises one or more of determining amounts, percentages, volumes or predictions of one or more levels of oxygen, nutrients, waste, electrolytes, glucose, urea, total proteins, bacteria, proteins, albumins, triglycerides, hematocrits, hemoglobins, complete blood count, circulating tumor cells, tumor markers CA 15.3 markers, TRU-QUANT and CA 27.29 markers, CA125 markers, CEA (carcino-embryonic antigen) markers, viruses, and pathologies associated with, contained in, or detectable in the body fluid sample.

88. The system of claim 73, wherein at least one of the tube or channel and frame or body comprises a polymer, a plastic and a polymeric material.

89. The system of claim 73, wherein polymer or plastic is at least one of anticoagulant-free, heparin-free, and comprises a polylactic acid (PLA) bioplastic.

90. The system of claim 73, wherein the cartridge is configured and shaped to place a top surface of the sheet, layer or membrane within about 0.4 mm and about 1.2 mm of the at least one aperture disposed in the spectroscopic device thereby to optimize signal-to-noise ratios of signals acquired by the spectroscopic device.

91. The system of claim 73, further comprising a cap, container or bag configured to seal at least portions of the cartridge to prevent contamination of the body fluid sample disposed therein.

92. The system of claim 73, further comprising or having associated therewith a machine-readable label or unique identifier comprising or providing access to information regarding the body fluid sample disposed in the cartridge.

93. The system of claim 73, wherein the cartridge is sized, shaped and configured for handling, processing, and analysis of the body fluid sample in a laboratory.

94. The system of claim 73, wherein the cartridge is configured and shaped for use with a corresponding wet or chemical analysis tube or receptacle.

95. The system of claim 73, wherein the cartridge is configured and shaped to permit the at least one sheet, layer or membrane to be cut or removed from the cartridge and extracted therefrom.

* * * * *